United States Patent
Bazargan et al.

(10) Patent No.: US 9,770,553 B2
(45) Date of Patent: Sep. 26, 2017

(54) MONITORING THE OPERATING HEALTH OF A FORCE SENSOR IN A FLUID INFUSION DEVICE

(71) Applicant: MEDTRONIC MINIMED, INC., Northridge, CA (US)

(72) Inventors: Afshin Bazargan, Simi Valley, CA (US); Pablo Vazquez, North Hills, CA (US); Hsiao-Yu S. Kow, Ladera Ranch, CA (US); Salman Monirabbasi, Playa Vista, CA (US); Ian B. Hanson, Wayne, PA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 818 days.

(21) Appl. No.: 14/095,091

(22) Filed: Dec. 3, 2013

(65) Prior Publication Data
US 2014/0094755 A1 Apr. 3, 2014

Related U.S. Application Data

(62) Division of application No. 12/976,591, filed on Dec. 22, 2010, now Pat. No. 8,628,510.

(51) Int. Cl.
*A61M 5/168* (2006.01)
*A61M 5/00* (2006.01)
*A61M 5/142* (2006.01)

(52) U.S. Cl.
CPC .......... *A61M 5/16854* (2013.01); *A61M 5/00* (2013.01); *A61M 5/14244* (2013.01);
(Continued)

(58) Field of Classification Search
CPC .............. A61M 5/142; A61M 5/14216; A61M 5/14244; A61M 5/14264; A61M 5/14566;
(Continued)

(56) References Cited

U.S. PATENT DOCUMENTS

| 3,631,847 A | 1/1972 | Hobbs, II |
| 4,080,653 A | 3/1978 | Barnes, Jr. et al. |

(Continued)

FOREIGN PATENT DOCUMENTS

| DE | 4329229 | 3/1995 |
| EP | 0319268 | 11/1988 |

(Continued)

OTHER PUBLICATIONS

PCT Search Report (PCT/US02/03299), Oct. 31, 2002, Medtronic MiniMed, Inc.

(Continued)

*Primary Examiner* — Kami A Bosworth
(74) *Attorney, Agent, or Firm* — Lorenz & Kopf, LLP

(57) ABSTRACT

A device for delivering fluid to a user includes a housing, a drive motor assembly in the housing, a force sensor, and an electronics module. The drive motor assembly regulates delivery of fluid by actuating a piston of a fluid reservoir, and the force sensor generates output levels in response to force imparted thereto during, for example, fluid delivery operations. The electronics module processes the output levels of the force sensor to assess the operating health of the force sensor, to check for occlusions in the fluid delivery path, and to monitor the seating status of the fluid reservoir.

8 Claims, 12 Drawing Sheets

(52) U.S. Cl.
CPC .......... *A61M 2005/16863* (2013.01); *A61M 2205/332* (2013.01)

(58) Field of Classification Search
CPC .......... A61M 5/168; A61M 5/16854; A61M 5/16859; A61M 2005/16863; A61M 2005/16872; A61M 2205/332
See application file for complete search history.

(56) References Cited

U.S. PATENT DOCUMENTS

| | | |
|---|---|---|
| 4,212,738 A | 7/1980 | Henne |
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,830,180 A | 11/1998 | Chandler et al. |
| 5,832,448 A | 11/1998 | Brown |
| 5,840,020 A | 11/1998 | Heinonen et al. |
| 5,861,018 A | 1/1999 | Feierbach |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,937,903 A | 8/1999 | Afshar et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,362,591 B1 | 3/2002 | Moberg |
| 6,408,330 B1 | 6/2002 | DeLaHuerga |

(56) References Cited

U.S. PATENT DOCUMENTS

| | | |
|---|---|---|
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,668,858 B1 | 12/2003 | Bazargan |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,193,521 B2 | 3/2007 | Moberg et al. |
| 7,396,330 B2 | 7/2008 | Banet et al. |
| 7,527,608 B2 | 5/2009 | Mason |
| 7,621,893 B2 | 11/2009 | Moberg et al. |
| 7,766,873 B2 | 8/2010 | Moberg et al. |
| 7,828,764 B2 | 11/2010 | Moberg et al. |
| 7,892,206 B2 | 2/2011 | Moberg et al. |
| 7,905,868 B2 | 3/2011 | Moberg et al. |
| 7,998,111 B2 | 8/2011 | Moberg et al. |
| 8,070,723 B2 | 12/2011 | Bazargan et al. |
| 8,182,447 B2 | 5/2012 | Moberg et al. |
| 8,197,444 B1 | 6/2012 | Bazargan et al. |
| 8,469,942 B2 | 6/2013 | Kow et al. |
| 8,556,856 B2 | 10/2013 | Bazargan et al. |
| 8,690,855 B2 | 4/2014 | Alderete, Jr. et al. |
| 2001/0034502 A1 | 10/2001 | Moberg et al. |
| 2001/0044731 A1 | 11/2001 | Coffman et al. |
| 2002/0013518 A1 | 1/2002 | West et al. |
| 2002/0043951 A1 | 4/2002 | Moberg |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0073954 A1 | 4/2003 | Moberg et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0085215 A1 | 5/2004 | Moberg et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0184154 A1 | 8/2006 | Moberg et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0100281 A1 | 5/2007 | Morris et al. |
| 2007/0135866 A1 | 6/2007 | Baker et al. |
| 2007/0149926 A1 | 6/2007 | Moberg et al. |
| 2007/0191770 A1* | 8/2007 | Moberg ............ A61M 5/14566 604/131 |
| 2007/0215235 A1* | 9/2007 | Ranalletta ............... B65B 3/003 141/2 |
| 2008/0154503 A1 | 6/2008 | Wittenber et al. |
| 2008/0221522 A1 | 9/2008 | Moberg et al. |
| 2008/0221523 A1 | 9/2008 | Moberg et al. |
| 2009/0081951 A1 | 3/2009 | Erdmann et al. |
| 2009/0082635 A1 | 3/2009 | Baldus et al. |
| 2010/0037680 A1 | 2/2010 | Moberg et al. |
| 2010/0164727 A1 | 7/2010 | Bazargan et al. |
| 2010/0168670 A1 | 7/2010 | Srisathapat et al. |
| 2010/0168711 A1 | 7/2010 | Bazargan et al. |
| 2011/0119033 A1 | 5/2011 | Moberg et al. |
| 2011/0160667 A1 | 6/2011 | Bazargan et al. |
| 2011/0224614 A1 | 9/2011 | Moberg et al. |
| 2012/0160033 A1 | 6/2012 | Kow et al. |
| 2012/0165733 A1 | 6/2012 | Bazargan et al. |
| 2012/0215169 A1 | 8/2012 | Moberg et al. |
| 2012/0215199 A1 | 8/2012 | Moberg et al. |
| 2012/0226234 A1 | 9/2012 | Bazargan et al. |
| 2012/0259282 A1 | 10/2012 | Alderete, Jr. et al. |
| 2013/0133438 A1 | 5/2013 | Kow et al. |
| 2013/0237953 A1 | 9/2013 | Kow et al. |
| 2013/0245595 A1 | 9/2013 | Kow et al. |

FOREIGN PATENT DOCUMENTS

| | | |
|---|---|---|
| EP | 0806738 | 11/1997 |
| EP | 0880936 | 12/1998 |
| EP | 0909911 A2 | 4/1999 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |

(56) References Cited

FOREIGN PATENT DOCUMENTS

| | | |
|---|---|---|
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |
| WO | WO 2009/102355 A2 | 8/2009 |
| WO | WO 2010078084 A2 | 7/2010 |

OTHER PUBLICATIONS (Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting A Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting A Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-TRON® plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.

(56) References Cited

OTHER PUBLICATIONS

Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.
Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.
Shichiri, Motoaki, et al., "Glycaemic Control in a Pacreatectomized Dogs with a Wearable Artificial Endocrine Pancreas," Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.
Shichiri, M., et al., "Membrane design for extending the long-life of an implantable glucose sensor," Diab. Nutr. Metab., vol. 2, No. 4, 1989, pp. 309-313.
Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.
Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.
Shichiri, Motoaki, et al., "Wearable Artificial Endocrine Pancreas with Needle-Type Glucose Sensor," The Lancet, Nov. 20, 1982, pp. 1129-1131.
Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.
Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.
Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.
Sternberg, Robert, et al., "Study and Development of Multilayer Needle-type Enzyme-based Glucose Microsensors," Biosensors, vol. 4, 1988, pp. 27-40.
Tamiya, E., et al., "Micro Glucose Sensors using Electron Mediators Immobilized on a Polypyrrole-Modified Electrode," Sensors and Actuators, vol. 18, 1989, pp. 297-307.
Tsukagoshi, Kazuhiko, et al., "Specific Complexation with Mono- and Disaccharides that can be Detected by Circular Dichroism," J. Org. Chem., vol. 56, 1991, pp. 4089-4091.
Urban, G., et al., "Miniaturized multi-enzyme biosensors integrated with pH sensors on flexible polymer carriers for in vivo applciations," Biosensors & Bioelectronics, vol. 7, 1992, pp. 733-739.
Ubran, G., et al., "Miniaturized thin-film biosensors using covalently immobilized glucose oxidase," Biosensors & Bioelectronics, vol. 6, 1991, pp. 555-562.
Velho, G., et al., "In vivo calibration of a subcutaneous glucose sensor for determination of subcutaneous glucose kinetics," Diab. Nutr. Metab., vol. 3, 1988, pp. 227-233.
Wang, Joseph, et al., "Needle-Type Dual Microsensor for the Simultaneous Monitoring of Glucose and Insulin," Analytical Chemistry, vol. 73, 2001, pp. 844-847.
Yamasaki, Yoshimitsu, et al., "Direct Measurement of Whole Blood Glucose by a Needle-Type Sensor," Clinics Chimica Acta, vol. 93, 1989, pp. 93-98.
Yokoyama, K., "Integrated Biosensor for Glucose and Galactose," Analytica Chimica Acta, vol. 218, 1989, pp. 137-142.

\* cited by examiner

MONITORING THE OPERATING HEALTH OF A FORCE SENSOR IN A FLUID INFUSION DEVICE

CROSS-REFERENCE TO RELATED APPLICATION(S)

This application is a divisional of U.S. patent application Ser. No. 12/976,591, filed Dec. 22, 2010, which issued on Jan. 14, 2014 as U.S. Pat. No. 8,628,510. The subject matter described herein is also related to the subject matter described in U.S. patent application Ser. No. 12/976,619, which issued on Jun. 12, 2012 as U.S. Pat. No. 8,197,444.

TECHNICAL FIELD

Embodiments of the subject matter described herein relate generally to medical devices. More particularly, embodiments of the subject matter relate to fluid infusion devices such as personal insulin infusion pumps.

BACKGROUND

Portable medical devices are useful for patients that have conditions that must be monitored on a continuous or frequent basis. For example, diabetics are usually required to modify and monitor their daily lifestyle to keep their blood glucose (BG) in balance. Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly.

The prior art includes a number of fluid infusion devices and insulin pump systems that are designed to deliver accurate and measured doses of insulin via infusion sets (an infusion set delivers the insulin through a small diameter tube that terminates at, e.g., a cannula inserted under the patient's skin). In lieu of a syringe, the patient can simply activate the insulin pump to administer an insulin bolus as needed, for example, in response to the patient's high BG level.

A typical infusion pump includes a housing, which encloses a pump drive system, a fluid containment assembly, an electronics system, and a power supply. The pump drive system typically includes a small motor (DC, stepper, solenoid, or other varieties) and drive train components such as gears, screws, and levers that convert rotational motor motion to a translational displacement of a stopper in a reservoir. The fluid containment assembly typically includes the reservoir with the stopper, tubing, and a catheter or infusion set to create a fluid path for carrying medication from the reservoir to the body of a user. The electronics system regulates power from the power supply to the motor. The electronics system may include programmable controls to operate the motor continuously or at periodic intervals to obtain a closely controlled and accurate delivery of the medication over an extended period.

Some fluid infusion devices use sensors and alarm features designed to detect and indicate certain operating conditions, such as non-delivery of the medication to the patient due to a fluid path occlusion. In this regard, a force sensor can be used in a fluid infusion device to detect when the force applied to the fluid reservoir stopper reaches a set point. The force sensor in such a fluid infusion device could be positioned at the end of the drive motor assembly that actuates a rotatable lead screw, which in turn advances the stopper of the reservoir. With such an arrangement, the force applied to the force sensor by the drive motor assembly is proportional to the pressure applied to the medication as a result of power supplied to the drive system to advance the stopper. Thus, when a certain force threshold (a set point corresponding to an occlusion condition) is reached, the fluid infusion device is triggered to generate an alarm to warn the user.

Early detection of an occlusion condition is helpful, because an occlusion can result in "under-dosing," particularly if the drive system continues to receive commands to deliver medication when the fluid path is blocked. Accordingly, proper operation of the force sensor is important for purposes of occlusion detection, and it is desirable to have some diagnostic capability related to the health of the force sensor.

Existing force-based occlusion detection techniques typically rely on a fixed threshold or set point that is indicative of an occlusion condition. A threshold value is selected based on system tolerances. To avoid frequent false alarms, however, it is necessary to set the threshold value above the maximum expected force, based on the interacting system components. Because the threshold value is set at the maximum expected force, if a patient has a particular pump system with a nominal delivery force, it may take slightly longer to reach the threshold force. Accordingly, it is desirable to have an occlusion detection technique that does not solely rely on a fixed occlusion detection threshold force.

Some fluid infusion devices use replaceable fluid reservoirs that are secured in the housing of the device and actuated by a drive assembly. One form of infusion pump utilizes a threaded cap to seat and secure the fluid reservoir in the housing of the pump. The user unscrews the threaded cap to remove an empty reservoir, replaces the old reservoir with a new reservoir, and reinstalls the threaded cap to secure the new reservoir in place. During use, the threaded cap might be dislodged (especially if the fluid infusion device is a portable unit that is worn by the patient), resulting in an unseated or improperly installed reservoir. For example, if the user participates in certain physical activities (e.g., sports, hiking, or rigorous exercise), then the cap might be unintentionally loosened by physical rotation. As another example, if the user is in a crowded environment (e.g., a concert, a nightclub, or a full elevator), then the cap might be inadvertently unscrewed through contact with another person or an object. For this reason, it is desirable to have a reservoir presence and/or seating detection technique for a fluid infusion pump.

BRIEF SUMMARY

A method of operating a fluid infusion device is provided. The fluid infusion device includes a drive motor assembly and a force sensor associated with the drive motor assembly. The method activates a rewind operation of the drive motor assembly and determines a rewind force imparted to the force sensor during the rewind operation. The method initiates corrective action for the fluid infusion device when the rewind force is less than a lower threshold force or greater than an upper threshold force.

Also provided is an exemplary embodiment of a device for delivering fluid to a user. The device includes: a housing; a drive motor assembly in the housing to regulate delivery of fluid by actuating a piston of a fluid reservoir; a force sensor associated with the drive motor assembly to generate output levels in response to force imparted thereto; and an electronics module coupled to the force sensor to process the output levels to determine operating health of the force sensor.

Another embodiment of a method of operating a fluid infusion device is also provided. The fluid infusion device includes a drive motor assembly and a force sensor associated with the drive motor assembly. The method involves determining a measure of actuation force imparted to the force sensor during a fluid delivery action of the drive motor assembly, and comparing the measure of actuation force against a range of valid values that represents normally expected measures of actuation forces. When the measure of actuation force is outside the range of valid values, the method initiates corrective action for the fluid infusion device.

A method of determining a seating status of a fluid reservoir in the reservoir cavity of a fluid infusion device is also provided. The fluid infusion device includes a drive motor assembly, a force sensor associated with the drive motor assembly, and a reservoir cavity that accommodates fluid reservoirs. The method begins by confirming initial seating of the fluid reservoir in the reservoir cavity. The method continues by determining a measure of actuation force imparted to the force sensor during a fluid delivery action of the drive motor assembly, and comparing the measure of actuation force to an amount of force that is less than normally expected actuation forces of the fluid infusion device, where the amount of force is indicative of an unseated state of the fluid reservoir. The method continues by initiating corrective action for the fluid infusion device when the measure of actuation force is less than the amount of force.

A device for delivering fluid to a user is also provided. The device includes: a housing; a reservoir cavity within the housing to accommodate fluid reservoirs; a drive motor assembly in the housing to regulate delivery of fluid by actuating a piston of a fluid reservoir; a force sensor associated with the drive motor assembly to generate output levels in response to force imparted thereto; and an electronics module coupled to the force sensor to process the output levels to determine a seating status of the fluid reservoir in the reservoir cavity.

Another embodiment of a method of determining a seating status of a fluid reservoir in the reservoir cavity of a fluid infusion device is provided. The method obtains baseline actuation force imparted to a force sensor, after initial seating and priming of the fluid reservoir. The method continues by determining a measured actuation force imparted to the force sensor, the measured actuation force corresponding to a designated delivery stroke of the drive motor assembly. The method also generates indicia of an unseated reservoir condition when the measured actuation force is less than the baseline actuation force by at least a predetermined amount of force.

Also provided is a method of determining a seating status of a fluid reservoir in a fluid infusion device having a drive motor assembly that actuates the fluid reservoir using discrete delivery pulses. The method obtains measures of actuation force imparted to the force sensor for a number of consecutive fluid delivery pulses, and calculates a pulse-to-pulse difference between consecutive fluid delivery pulses, the pulse-to-pulse difference based on respective measures of actuation force for the consecutive fluid delivery pulses. The method continues by initiating corrective action for the fluid infusion device when the pulse-to-pulse difference is greater than a threshold force value.

Another embodiment of a method of determining a seating status of a fluid reservoir in a fluid infusion device is provided. The infusion device has a drive motor assembly that actuates the fluid reservoir using discrete delivery pulses, and the method involves: maintaining a count that is indicative of the seating status; storing an adaptive reference force value that corresponds to a previously recorded measure of actuation force imparted to the force sensor during a previous fluid delivery pulse; obtaining a current measure of actuation force imparted to the force sensor for a current fluid delivery pulse; changing the count when the current measure of actuation force is less than the difference between the adaptive reference force value and a threshold force value, resulting in an updated count; and generating a seating status alert when the updated count satisfies predetermined alert criteria.

According to various embodiments, provided is a device for delivering fluid to a user. The device includes a housing and a drive motor assembly in the housing to regulate delivery of fluid by actuating a piston of a fluid reservoir. The device also includes a force sensor associated with the drive motor assembly to generate output levels in response to force imparted thereto, and an electronics module coupled to the force sensor to process the output levels to determine if the fluid reservoir is seated within the housing.

Also provided according to various embodiments is a device for delivering fluid to a user. The device includes a housing and a drive motor assembly in the housing to regulate delivery of fluid by actuating a piston of a fluid reservoir. The device includes a force sensor associated with the drive motor assembly to generate output levels in response to force imparted thereto. The force sensor is disposed in the housing between the drive motor assembly and a portion of the housing. The device includes an electronics module coupled to the force sensor to process the output levels to determine a rewind force imparted to the force sensor during a rewind operation. The electronics module initiates corrective action when the rewind force is not within a specified range.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
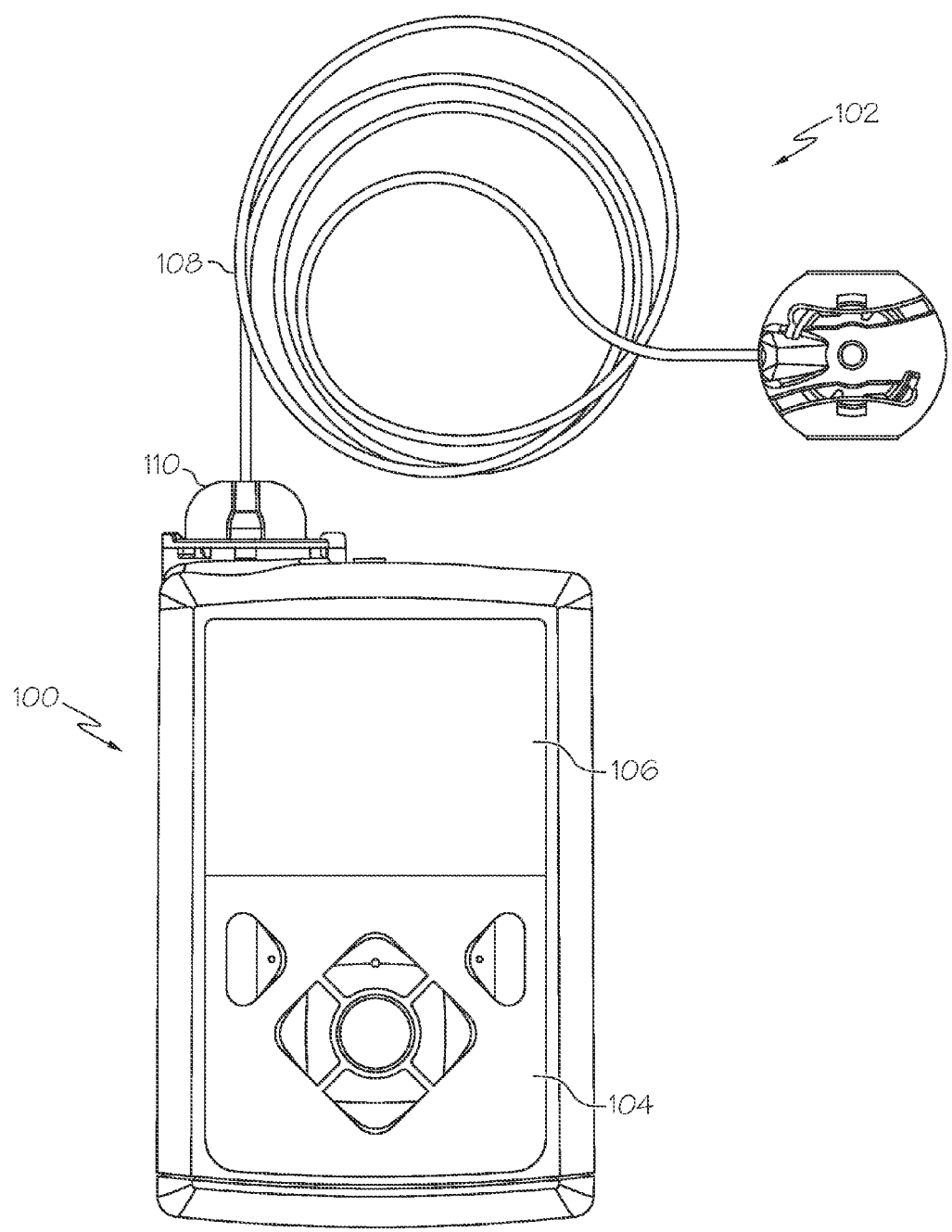
FIG. 1 is a schematic representation of an embodiment of a fluid infusion device.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

For the sake of brevity, conventional techniques related to infusion system operation, insulin pump and/or infusion set operation, blood glucose sensing and monitoring, force sensors, signal processing, and other functional aspects of the systems (and the individual operating components of the systems) may not be described in detail here. Examples of infusion pumps and/or related pump drive systems used to administer insulin and other medications may be of the type described in, but not limited to, U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; and 7,621,893; which are herein incorporated by reference.

The subject matter described here relates to a fluid infusion device of the type used to treat a medical condition of a patient. The infusion device is used for infusing fluid into the body of a user. The non-limiting examples described below relate to a medical device used to treat diabetes (more specifically, an insulin pump), although embodiments of the disclosed subject matter are not so limited. Accordingly, the infused fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like.

A methodology for monitoring the operational health of a sensor (e.g., a force sensor) is implemented by an exemplary embodiment of a fluid infusion device. The fluid infusion device monitors force measurements obtained from the force sensor during a motor rewind operation to determine whether or not the force sensor might be out of calibration, on the verge of failure, or the like. The force normally experienced by the force sensor during rewind operations should be zero or close to zero, due to the absence of a fluid reservoir in the fluid infusion device, and because the fluid infusion device is driving in rewind mode, i.e., away from the plunger of the fluid reservoir. Accordingly, the fluid infusion device can assume that a properly functioning force sensor will produce rewind force readings in the neighborhood of zero or close to zero. Thus, if a rewind force measurement significantly deviates from the assumed baseline value (or range of values), then the fluid infusion device can take appropriate corrective action.

Another methodology for monitoring the operational health of a force sensor obtains force readings during a fluid delivery operation and compares the force readings to determine whether or not the force sensor is operating as expected. This alternate methodology measures the forces associated with individual fluid delivery strokes or drive motor pulses. Under normal and typical operating conditions, these forces will be relatively stable during one fluid delivery operation, and the variation from one stroke to another will be slight (absent an external impact or shock suffered by the fluid infusion device). Thus, if the force sensor reading is out of the expected operating range during a fluid delivery operation, the fluid infusion device can take appropriate corrective action. For example, if the force sensor output during fluid delivery happens to be −0.5 pounds, then clearly there is a problem because in reality the measured force should not be a negative value.

A fluid infusion device may also have an occlusion detection feature that determines when the fluid delivery path is occluded. Occlusion detection techniques are usually based on sensor measurements (force, pressure, stress) that are influenced by the flow status of the fluid delivery path. An exemplary embodiment of a fluid infusion device as described here employs an adaptive occlusion detection technique that need not rely on a fixed occlusion detection force threshold. Instead, the adaptive occlusion detection technique evaluates the rate of change of a metric associated with force variations per units of fluid to be delivered. For example, the typical force variation for a fluid reservoir might result in a variation of about ±X pounds per unit (lb/U) over a set number of delivery strokes (or drive motor pulses). If, however, the fluid infusion device detects a significant increase in this metric during a fluid delivery operation (e.g., ±Y lb/U, where Y is significantly larger than X) over the same set number of delivery strokes, then the fluid infusion device can take appropriate corrective action. The values of X and Y can also be in units of lb/pulse or the like. An example of a corrective action might be, but not limited to, immediately indicate or warn of an occlusion or simply lower the set threshold value by a set constant or percentage and allow the pump to continue delivery for a set number of pulses or units to see if the pump recovers (recovery might occur in the case of a kinked cannula). The adaptive occlusion detection methodology allows the fluid infusion device to determine the existence of an occlusion much quicker, relative to a fixed threshold based methodology. Quicker occlusion detection is made possible because the fluid infusion device need not be operated until a high threshold force is reached; rather, occlusion can be detected earlier without having to wait for a high force condition.

An exemplary embodiment of a fluid infusion device may also be configured to determine whether or not a fluid reservoir is properly seated and installed. The presence (or lack thereof) of the fluid reservoir is determined based upon force sensor readings that are obtained after proper initial installation and seating of the fluid reservoir. In accordance with one embodiment, one or more force thresholds are used to determine whether or not the fluid reservoir is properly seated. If a measured force does not satisfy a force threshold that is indicative of proper reservoir seating, then the fluid infusion device can take corrective action. In accordance with another exemplary embodiment, the fluid infusion device measures and processes the forces associated with individual fluid delivery strokes or drive motor pulses to determine when the fluid reservoir has been dislodged, removed, or unseated.

FIG. 1 is a plan view of an exemplary embodiment of a fluid infusion device 100. FIG. 1 also shows an infusion set 102 coupled to the fluid infusion device 100. The fluid infusion device 100 is designed to be carried or worn by the patient. The fluid infusion device 100 may leverage a number of conventional features, components, elements, and characteristics of existing fluid infusion devices. For example, the fluid infusion device 100 may incorporate some of the features, components, elements, and/or characteristics described in U.S. Pat. Nos. 6,485,465 and 7,621,893, the relevant content of which is incorporated by reference herein.

This embodiment shown in FIG. 1 includes a user interface 104 that includes several buttons that can be activated by the user. These buttons can be used to administer a bolus of insulin, to change therapy settings, to change user preferences, to select display features, and the like. Although not required, the illustrated embodiment of the fluid infusion device 100 includes a display element 106. The display element 106 can be used to present various types of information or data to the user, such as, without limitation: the current glucose level of the patient; the time; a graph or chart of the patient's glucose level versus time; device status indicators; etc. In some embodiments, the display element 106 is realized as a touch screen display element and, therefore, the display element 106 also serves as a user interface component.

The fluid infusion device 100 accommodates a fluid reservoir (hidden from view in FIG. 1) for the fluid to be delivered to the user. A length of tubing 108 is the flow path that couples the fluid reservoir to the infusion set 102. The tubing 108 extends from the fluid infusion device 100 to the infusion set 102, which provides a fluid pathway with the body of the user. A removable cap or fitting 110 is suitably sized and configured to accommodate replacement of fluid reservoirs (which are typically disposable) as needed. In this regard, the fitting 110 is designed to accommodate the fluid path from the fluid reservoir to the tubing 108.

Figure 2:
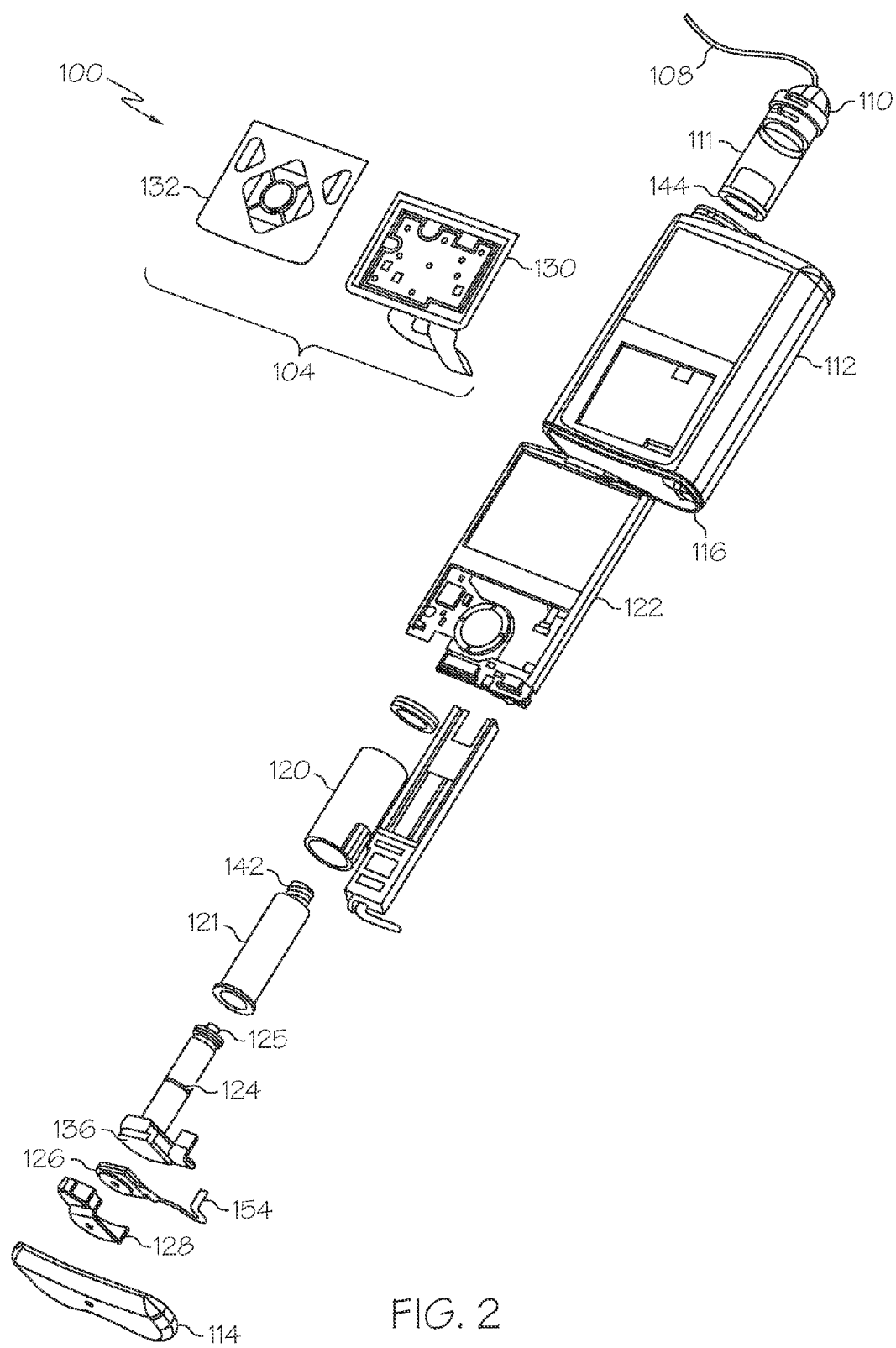
FIG. 2 is an exploded perspective view of the fluid infusion device shown in FIG. 1.

FIG. 2 is an exploded perspective view of the fluid infusion device 100. For the sake of brevity and simplicity, FIG. 2 is a simplified depiction of the fluid infusion device 100 that does not include all of the elements, components, and features that would otherwise be present in a typical embodiment. It should be appreciated that a deployed implementation of the fluid infusion device 100 will include additional features, components, and elements that are not shown in the figures.

The embodiment of the fluid infusion device 100 illustrated in FIG. 2 includes a housing 112 and a housing end cap 114 that is coupled to an end 116 of the housing 112 to enclose components within the housing 112. These internal components include, without limitation: a battery tube subassembly 118; a sleeve 120; a slide 121; an electronics assembly 122; a drive motor assembly 124 having a drive screw 125; a force sensor 126; and a motor support cap 128. FIG. 2 also depicts some components that are located outside the housing 112, namely, a keypad assembly 130 and a graphic keypad overlay 132 for the keypad assembly 130. The keypad assembly 130 and the graphic keypad overlay 132 may be considered to be part of the user interface 104 of the fluid infusion device 100. The outer edge of the motor support cap 128 is attached to the interior side of the housing 112, and the motor support cap 128 contacts the force sensor 126 to remove assembly tolerances from the drive motor assembly 124. FIG. 2 also depicts an exemplary fluid reservoir 111, which is inserted into a reservoir cavity defined within the housing 112. The reservoir cavity is configured, sized, and shaped to accommodate fluid reservoirs, and the fluid reservoir 111 is maintained in the reservoir cavity using the fitting 110. The electronics assembly 122 may include a suitably configured electronics module (not shown in FIG. 2; see FIG. 4 and related description below), which may include or cooperate with a power supply, at least one memory element, at least one processor, processing logic, and device software, firmware, and application programs.

Figure 3:
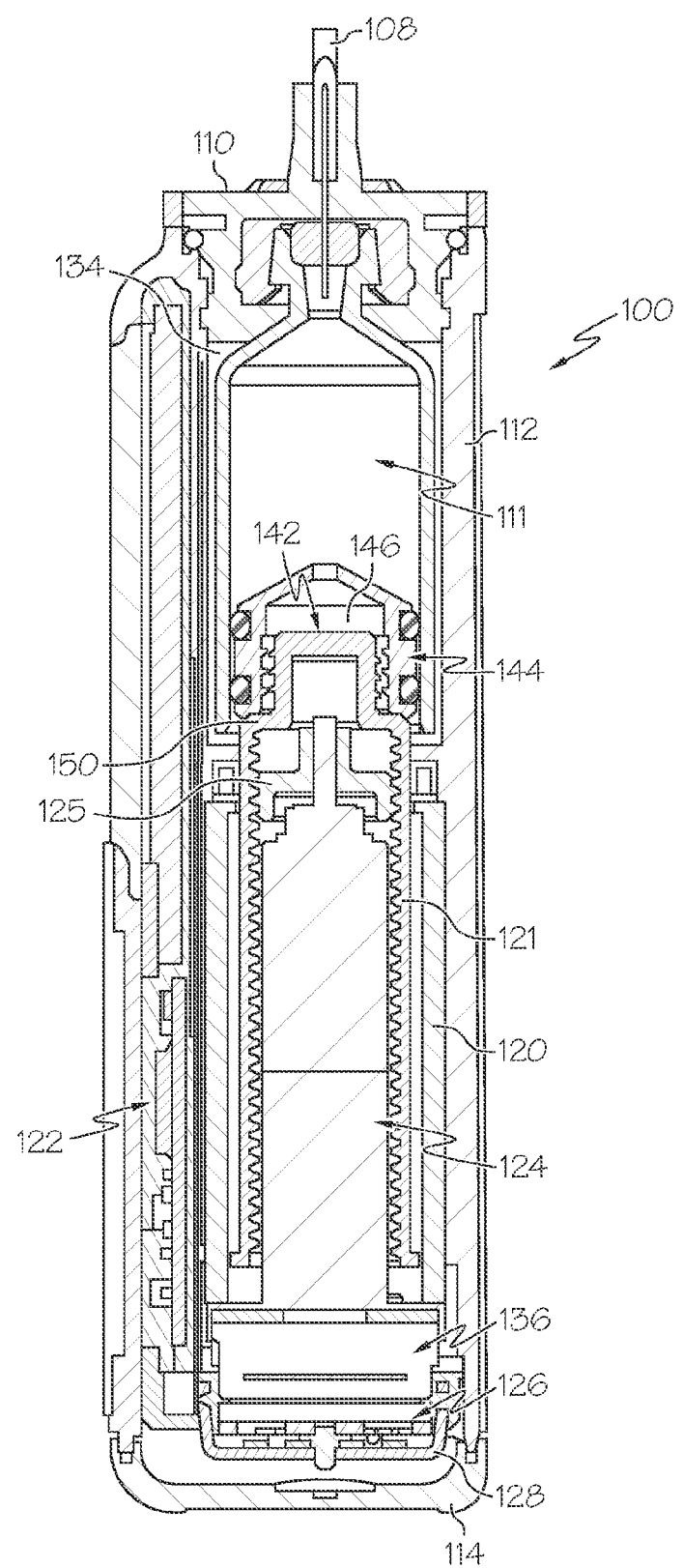
FIG. 3 is a cross sectional view of the fluid infusion device shown in FIG. 1, corresponding to a cross section taken longitudinally through the drive motor assembly and the fluid reservoir.

FIG. 3 is a cross sectional view of the fluid infusion device 100, corresponding to a cross section taken longitudinally through the drive motor assembly 124 and the fluid reservoir 111. FIG. 3 depicts the state of the fluid infusion device 100 after the fluid reservoir 111 has been inserted into the reservoir cavity 134 and after the fitting 110 has been secured to the housing 112 to hold the fluid reservoir 111 in place. While certain embodiments accommodate disposable, prefilled reservoirs, alternative embodiments may use refillable cartridges, syringes or the like. A cartridge can be prefilled with insulin (or other drug or fluid) and inserted into the housing 112. Alternatively, a cartridge could be filled by the user using an appropriate adapter and/or any suitable refilling device.

When assembled as shown in FIG. 3, the drive motor assembly 124 is located in the housing 112. The force sensor 126 is operatively associated with the drive motor assembly 124. For this particular embodiment, the force sensor 126 is coupled to the drive motor assembly 124, and it is located between a base end of the drive motor assembly 124 and the motor support cap 128. In one implementation, the force sensor 126 is affixed to the base end of the drive motor assembly 124 such that the force sensor 126 reacts when it bears against the motor support cap 128. In another implementation, the force sensor 126 is affixed to the housing end cap 114 such that the force sensor 126 reacts when the drive motor assembly 124 bears against the force sensor 126. This configuration and arrangement of the drive motor assembly 124 and the force sensor 126 allows the force sensor 126 to react to forces imparted thereto by the drive motor assembly 124 and/or forces imparted to the drive motor assembly 124 via the fluid pressure of the fluid reservoir 111.

The drive motor assembly 124 includes an electric motor 136 that is actuated and controlled by the electronics module of the fluid infusion device 100. The motor 136 is preferably realized as a stepper motor that rotates in a stepwise or discrete manner corresponding to the desired number of fluid delivery strokes. Alternatively, the motor 136 could be a DC motor, a solenoid, or the like. The motor 136 may optionally include an encoder (not shown), which cooperates with the electronics module of the fluid infusion device 100 to monitor the number of motor rotations or portions thereof. This in turn can be used to accurately determine the position of the slide 121, thus providing information relating to the amount of fluid dispensed from the fluid reservoir 111.

The drive motor assembly 124 can be mounted in the housing 112 using an appropriate mounting feature, structure, or element. Alternatively, the mounting could be accomplished using a shaft bearing and leaf spring or other known compliance mountings.

The illustrated embodiment of the drive motor assembly 124 includes a drive member (such as the externally threaded drive gear or drive screw 125) that engages an internally threaded second drive member (such as the slide 121) having a coupler 142. The coupler 142 may be attached to or integrated with the slide 121, as depicted in FIG. 2 and FIG. 3. The slide 121 is sized to fit within the housing of the fluid reservoir 111, which enables the slide 121 to operatively cooperate with the fluid reservoir 111. The fluid reservoir 111 includes a plunger or piston 144 with at least one sealing element or feature (e.g., one or more O-rings, integral raised ridges, or a washer) for forming a fluid and air tight seal with the inner wall of the fluid reservoir 111. As mentioned previously, the fluid reservoir 111 is secured into the housing 112 with the fitting 110, which also serves as the interface between the fluid reservoir 111 and the infusion set tubing 108. For this embodiment, the piston 144 is in contact with a linear actuation member, such as the slide 121. For example, the piston 144 may have a female portion 146 that receives the coupler 142 carried by the slide 121. The female portion 146 is positioned at the end face of the piston 144, and it is sized to receive and accommodate the coupler 142. In certain embodiments, the female portion 146 includes a threaded cavity that engages external threads of the coupler 142.

Referring to FIG. 3, rotation of the drive shaft of the motor 136 results in corresponding rotation of the drive screw 125, which in turn drives the slide 121 via the threaded engagement. Thus, rotation of the drive screw 125 results in axial displacement of the slide 121 and, therefore, axial displacement of the coupler 142. Such displacement of the coupler 142 moves the piston 144 (upward in FIG. 3) to deliver a predetermined or commanded amount of medication or liquid from the fluid infusion device 100. In this manner, the drive motor assembly 124 is configured to regulate delivery of fluid by actuating the piston 144 (under the control of the electronics module and/or control system of the fluid infusion device 100). As described above, if a stepper motor is employed, then the drive motor assembly 124 can regulate delivery of fluid from the fluid infusion device 100 in discrete actuation or delivery strokes. The fluid infusion device 100 can employ the sleeve 120 or an equivalent feature (such as an anti-rotation key) to inhibit rotation of the drive motor assembly 124, which might otherwise result from torque generated by the motor 136. In some embodiments, the drive shaft of the drive motor assembly 124, the drive screw 125, and the slide 121 are all coaxially centered within the longitudinal axis of travel of the piston 144. In certain alternative embodiments, one or more of these components may be offset from the center of the axis of travel and yet remain aligned with the axis of travel, which extends along the length of the fluid reservoir 111.

As mentioned above, certain embodiments of the fluid infusion device 100 accommodate removable and replaceable fluid reservoirs. When the slide 121 and, therefore, the piston 144 of the fluid reservoir 111 are in their fully extended positions, the piston 144 has forced most, if not all, of the fluid out of the fluid reservoir 111. After the piston 144 has reached the end of its travel path, indicating that the fluid reservoir 111 has been depleted, the fluid reservoir 111 may be removed such that the female portion 146 of the piston 144 disengages from the coupler 142 of the slide 121. After the empty (or otherwise used) fluid reservoir 111 is removed, the electronics module or control system of the fluid infusion device 100 initiates a rewind operation during which the motor 136 rotates in the reverse direction to rewind the slide 121 back to its fully retracted position. Thereafter, a new or refilled fluid reservoir 111 can be installed, seated, and primed for use. In this regard, an embodiment provides for advancement of the slide 121 upon the insertion of a fluid reservoir 111 into the housing 112. The slide 121 advances until its coupler 142 comes into contact with the piston 144 of the fluid reservoir 111. In alternative embodiments having a threaded piston engagement, the slide 121 advances until the threads of the coupler 142 engage the threads in the female portion 146 of the piston 144. When the threads engage in this fashion, they need not do so by twisting. Rather, they may ratchet over one another. In operation, the force sensor 126 may be used to determine when the slide 121 contacts the piston 144, when the coupler 142 is properly seated in the female portion 146, and/or when the fluid reservoir 111 has been primed and is ready to deliver measured doses of fluid.

Although the illustrated embodiment employs a coaxial or inline drive system, alternative configurations could be utilized. For example, a drive system that uses a lead screw, a drive nut, and actuation arms (of the type described in U.S. Pat. No. 6,485,465) may be employed, with the force sensor 126 positioned in an appropriate location. In various embodiments, the drive train might include one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. Moreover, although the illustrated embodiment employs a sensor positioned at the end of the fluid drive train, other arrangements could be deployed. For example, a sensor could be placed at or near the front end of the fluid drive train.

In particular embodiments, the force sensor 126 is used to detect when the slide 121 contacts the piston 144. Thus, after the fluid reservoir 111 is placed into the fluid infusion device 100, the motor 136 is activated to move the slide 121 toward the fluid reservoir 111 to engage the piston 144. In this regard, when a shoulder region 150 (see FIG. 3) of the slide 121 first contacts the piston 144, the electronics module detects an increase in force imparted to the force sensor 126. The measured force continues to increase as the motor 136 continues to drive forward, in response to the fluid resistance in the fluid reservoir 111. When the slide 121 is properly seated with the piston 144, the measured force increases to the seating threshold level. During the seating operation, if the measured force exceeds this seating threshold, the motor 136 is stopped until further commands are issued. The seating threshold is generally about 1.5 pounds. In alternative embodiments, higher or lower seating thresholds may be used depending on the force required to mate the slide 121 with the piston 144, the force required to urge fluid from the fluid reservoir 111, the speed of the motor 136, the accuracy and resolution of the force sensor 126, or the like.

It should be appreciated that other force thresholds can be used for other purposes. During priming of fluid reservoirs, for example, a threshold of about 4.0 pounds is used. In some embodiments, levels greater than about 5.0 pounds are used to detect shock loads that may be damaging to the fluid infusion device 100.

The force sensor 126 is configured to react in response to force imparted thereto. In this regard, electrical, mechanical, magnetic, and/or other measurable or detectable characteristics of the force sensor 126 vary in accordance with the amount of force applied to the force sensor 126. In practice, the force sensor 126 might implement or otherwise leverage known sensor technologies, such as the sensor technology described in U.S. Pat. No. 6,485,465. As shown in FIG. 2, the force sensor 126 includes at least one electrical lead 154 that is electrically coupled to the electronics module (or controller) of the fluid infusion device 100. Alternatively, the force sensor 126 could use wireless data communication technology to provide force-related data to the electronics module. In certain implementations, the force sensor 126 is suitably configured to indicate or generate a plurality of different output levels that can be monitored and/or determined by the electronics module. In practice, the output levels obtained from the force sensor 126 are initially conveyed as analog voltages or analog currents, and the electronics module includes an analog-to-digital converter that transforms a sampled analog voltage into a digital representation. Conversion of sensor voltage into the digital domain is desirable for ease of processing, comparison to threshold values, and the like.

In particular embodiments, the force sensor 126 is realized as an electromechanical component having at least one variable resistance that changes as the force applied to the force sensor 126 changes. In alternative embodiments, the force sensor 126 is a capacitive sensor, a piezoresistive sensor, a piezoelectric sensor, a magnetic sensor, an optical sensor, a potentiometer, a micro-machined sensor, a linear transducer, an encoder, a strain gauge, or the like, and the detectable parameter or characteristic might be compression, shear, tension, displacement, distance, rotation, torque, force, pressure, or the like. In practice, changing characteristics of the force sensor 126 are associated with output signal characteristics that are responsive to a physical parameter to be measured. Moreover, the range and resolution of the monitored output signal provides for the desired number of output levels (e.g., different states, values, quantities, signals, magnitudes, frequencies, steps, or the like) across the range of measurement. For example, the force sensor 126 might generate a low or zero value when the applied force is relatively low, a high or maximum value when the applied force is relatively high, and intermediate values when the applied force is within the detectable range.

In certain exemplary embodiments, the electronics module of the fluid infusion device 100 maintains a constant supply voltage across the force sensor 126, and the monitored output signal of the force sensor 126 is a signal current that passes through a resistive material of the force sensor 126. Thus, the signal current varies with the amount of force applied to the force sensor 126 because the resistance of the force sensor 126 varies with force and the supply voltage across the force sensor 126 is constant. The electronics module converts the monitored signal current into a signal voltage, which is then used as an indication of the force imparted to the force sensor 126 (which may be caused by the drive motor assembly 124, by fluid pressure in the fluid reservoir 111, by impact experienced by the fluid infusion device 100, etc.). In alternative embodiments, a constant supply current is used and the signal voltage across the force sensor 126 varies with force (fluid pressure).

In certain embodiments, sensor measurements are taken prior to commanding the drive system to deliver fluid, and soon after the drive system has stopped delivering fluid. In alternative embodiments, sensor data is collected on a continuous basis at a particular sampling rate (for example, 10.0 Hz, 3.0 Hz, once every 10 seconds, once a minute, once every five minutes, or the like). In further alternative embodiments, the sensor data is only collected prior to commanding the drive system to deliver fluid. In still further alternative embodiments, sensor data is collected during fluid delivery (during delivery strokes and/or between delivery strokes).

In practice, the force sensor 126 and associated electronics are designed to measure forces between about zero pounds and about five pounds with a desired resolution of about 0.01 pounds. In preferred embodiments, the force sensor 126 and associated electronics provide a relatively linear voltage output in response to forces applied to the force sensor 126 by one or more drive train components. In alternative embodiments, the range and resolution of the force sensor 126 might vary from that specified above. Furthermore, the sensor range and/or resolution may vary in accordance with the concentration of the fluid being delivered, the diameter of the fluid reservoir 111, the diameter of the fluid path, the nominal range of force experienced during normal operation of the drive motor assembly 124, the amount of sensor noise, the algorithms applied to detect trends from sensor measurements, or the like. Moreover, the fluid infusion device 100 and the force sensor 126 should be suitably configured to survive shock levels that result in much higher forces being applied to the force sensor 126 than the intended sensor measurement range.

Figure 4:
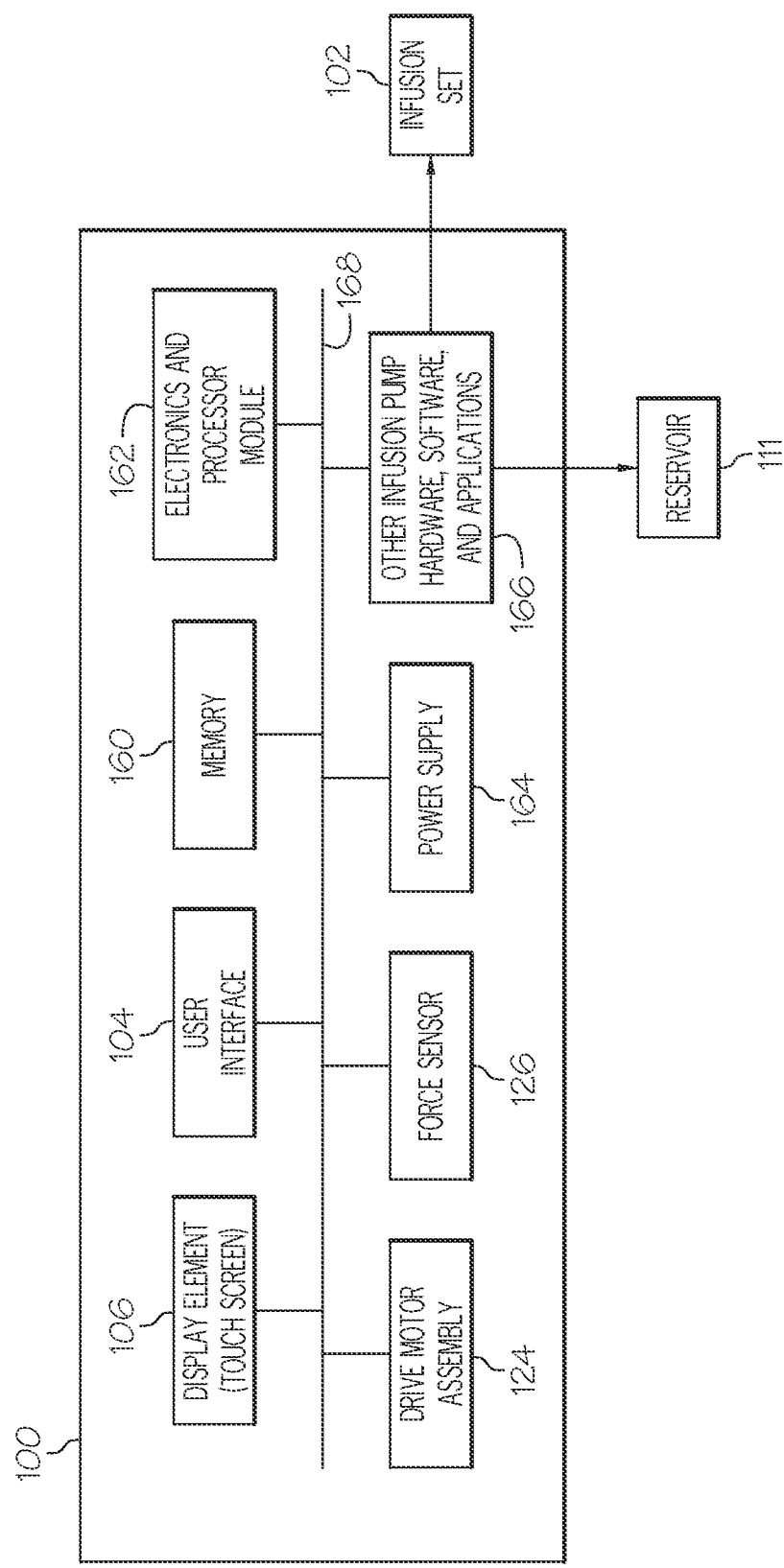
FIG. 4 is a schematic block diagram representation of an embodiment of a fluid infusion device.

As mentioned previously, the fluid infusion device 100 is suitably configured to support a number of techniques, processes, and methodologies that utilize the force sensor 126. In practice, the fluid infusion device 100 includes an electronics module, processing logic, software applications, and/or other features that are used to carry out the various operating processes described here. In this regard, FIG. 4 is a schematic block diagram representation of an embodiment of the fluid infusion device 100. FIG. 4 depicts some previously-described elements of the fluid infusion device 100 as functional blocks or modules, namely, the display element 106; the user interface 104; the drive motor assembly 124; and the force sensor 126. FIG. 4 also depicts the fluid reservoir 111 and the infusion set 102 in block format. This particular embodiment of the fluid infusion device 100 also includes, without limitation: a suitable amount of memory 160; an electronics module 162 (which may include or cooperate with one or more processors, processing modules, controllers, state machines, or the like); a power supply 164 such as a battery or a battery pack; and other infusion pump hardware, software, and applications 166. The elements of the fluid infusion device 100 may be coupled together via an interconnection architecture 168 or arrangement that facilitates transfer of data, commands, power, etc.

The display element 106 represents the primary graphical interface of the fluid infusion device 100. The display element 106 may leverage known plasma, liquid crystal display (LCD), thin film transistor (TFT), and/or other display technologies. The actual size, resolution, and operating specifications of the display element 106 can be selected to suit the needs of the particular application. Notably, the display element 106 may include or be realized as a touch screen display element that can accommodate touch screen techniques and technologies. In practice, the display element 106 may be driven by a suitable display driver to enable the fluid infusion device 100 to display physiological patient data, status information, clock information, alarms, alerts, and/or other information and data received or processed by the fluid infusion device 100.

The user interface 104 may include a variety of items such as, without limitation: a keypad, keys, buttons, a keyboard, switches, knobs (which may be rotary or push/rotary), a touchpad, a microphone suitably adapted to receive voice commands, a joystick, a pointing device, an alphanumeric character entry device or touch element, a trackball, a motion sensor, a lever, a slider bar, a virtual writing tablet, or any device, component, or function that enables the user to select options, input information, or otherwise control the operation of the fluid infusion device 100. In this context, the user interface 104 may cooperate with or include a touch screen display element 106. The user interface 104 allows a user to control the delivery of fluid via the infusion set 102.

The electronics module 162 may include or be implemented with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. A processor device may be realized as a microprocessor, a controller, a microcontroller, or a state machine. Moreover, a processor device may be implemented as a combination of computing devices, e.g., a combination of a digital signal processor and a microprocessor, a plurality of microprocessors, one or more microprocessors in conjunction with a digital signal processor core, or any other such configuration.

The electronics module 162 may include one processor device or a plurality of cooperating processor devices. Moreover, a functional or logical module/component of the fluid infusion device 100 might be realized by, implemented with, and/or controlled by processing logic maintained by or included with the electronics module 162. For example, the display element 106, the user interface 104, the drive motor assembly 124, and/or the infusion pump hardware, software, and applications 166 (or portions thereof) may be implemented in or controlled by the electronics module 162.

The memory 160 may be realized as RAM memory, flash memory, EPROM memory, EEPROM memory, registers, a hard disk, a removable disk, a CD-ROM, or any other form of storage medium known in the art. In this regard, the memory 160 can be coupled to the electronics module 162 such that the electronics module 162 can read information from, and write information to, the memory 160. In the alternative, the memory 160 may be integral to the electronics module 162. As an example, a processor of the electronics module 162 and the memory 160 may reside in an ASIC. In practice, a functional or logical module/component of the fluid infusion device 100 might be realized using program code that is maintained in the memory 160. Moreover, the memory 160 can be used to store data utilized to support the operation of the fluid infusion device 100, including, without limitation, sensor data, force measurements, force thresholds, alert/alarm history, and the like (as will become apparent from the following description).

The infusion pump hardware, software, and applications 166 are utilized to carry out fluid infusion features, operations, and functionality. Thus, the infusion pump hardware, software, and applications 166 may include or cooperate with the infusion set 102 and/or the fluid reservoir 111 (as described above). It should be appreciated that the infusion pump hardware, software, and applications 166 may leverage known techniques to carry out conventional infusion pump functions and operations, and such known aspects will not be described in detail here.

A fluid infusion device can support one or more features or operations that enhance its fluid infusion functionality and/or enhance the user experience of the fluid infusion device. The following sections include descriptions of various processes and methods that may be performed by a fluid infusion device. The various tasks performed in connection with a given process may be performed by software, hardware, firmware, or any combination thereof. For illustrative purposes, a process might be described with reference to elements mentioned above in connection with FIGS. 1-4. In practice, portions of a given process may be performed by different elements of the described system, e.g., a sensor, a drive motor assembly, an electronics module, a processor, or the like. It should be appreciated that a described process may include any number of additional or alternative tasks, the tasks included in a particular flow chart need not be performed in the illustrated order, an embodiment of a described process may omit one or more of the illustrated tasks, and a given process may be incorporated into a more comprehensive procedure or process having additional functionality not described in detail herein.

Sensor Health Monitoring

For reasons presented above, the force sensor 126 in the fluid infusion device 100 is an important component that, at a minimum, is used to determine when a new fluid reservoir 111 is seated and when an occlusion has occurred. During use, the output and/or electromechanical characteristics of the force sensor 126 may drift over time. The drift can be attributed to the aging of mechanical components, impacts or shocks suffered by the fluid infusion device 100, environmental exposure, etc. It is desirable to monitor sensor drift so that the fluid infusion device 100 can alert the patient if the sensor drift exceeds a tolerable amount. Notably, the force sensor 126 cannot be easily or conveniently calibrated, for example on a yearly basis, because it is not accessible. Consequently, the force sensor 126 should not divert from a calibration curve (which contemplates typical variations or drifting of the force sensor 126) over the life of the product.

The sensor health monitoring features of the fluid infusion device 100 can be utilized to determine and monitor the drift characteristics of the force sensor 126. In accordance with one approach, it is assumed that the force sensor 126 experiences a consistent and relatively low load during rewind operations, which are performed before installing a new fluid reservoir 111. During a calibration routine (which may be performed, for example, during manufacturing of the fluid infusion device 100), the device records force data collected during one or more rewind stages. The force data is used to generate a nominal rewind force value, which may represent an average of the collected values, the maximum collected value, the minimum collected value, or the like. This rewind force value is saved in the memory 160 of the fluid infusion device 100. Thereafter, when deployed and operating, the fluid infusion device 100 performs a rewind force average check and compares the value to the saved rewind force. If the measured rewind force is within a specified range of the calibration rewind force value, then the fluid infusion device 100 continues to operate as usual. If, however, the measured rewind force drifts below a level that is not acceptable, then the fluid infusion device 100 can generate an alarm, an alert, or respond in a predetermined manner. The sensor health can be checked whenever a new fluid reservoir 111 is installed, typically every three days.

Figure 5:
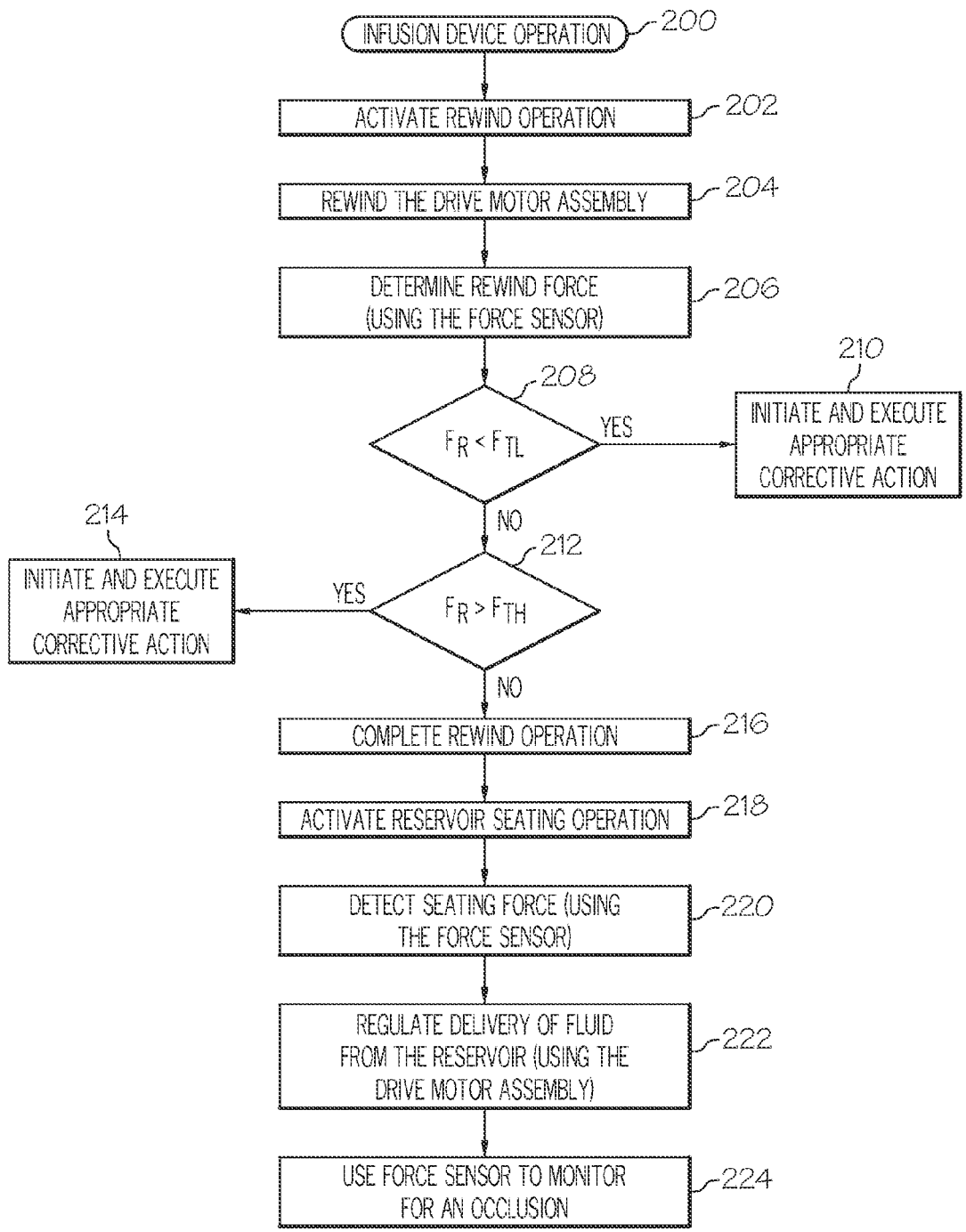
FIG. 5 is a flow chart that illustrates an embodiment of a process associated with the operation of a fluid infusion device.

FIG. 5 is a flow chart that illustrates an embodiment of a process 200 associated with the operation of a fluid infusion device, such as the fluid infusion device 100 described above. The process 200 may begin with the activation of a rewind operation of the drive motor assembly (task 202). As explained above, the drive motor assembly rewinds after removing an old fluid reservoir and before installing a new fluid reservoir. Accordingly, task 202 could be automatically performed whenever a fluid reservoir is removed from the fluid infusion device. As another option, task 202 could be performed (either automatically or initiated by the user) at other times when the fluid infusion device 100 is not delivering fluid. In this regard, the slide 121 can be retracted from the piston 144 while leaving the piston 144 in place. The position of the slide 121 prior to retraction can be stored such that the slide 121 can be precisely returned to its former position to continue delivering fluid. In response to the rewind activation, the process 200 rewinds the drive motor assembly by an appropriate amount (task 204). To accommodate installation of a new fluid reservoir, task 204 rewinds the drive motor assembly until the slide is fully retracted.

The absence of a fluid reservoir during the rewind operation results in no loading on the drive motor assembly. For this reason, the process 200 determines a rewind force imparted to the force sensor during the rewind operation (task 206). Task 206 could obtain a single rewind force measurement at any time during the rewind operation, it could calculate an average rewind force based upon any number of rewind force measurements obtained during the rewind operation, or it could generate any rewind force value or metric that is based upon one or more individual rewind force measurements obtained during the rewind operation. For simplicity, this particular embodiment of the process 200 assumes that a single rewind force measurement is determined at task 206.

The process 200 may continue by comparing the rewind force measurement to one or more threshold forces. For this example, the process 200 determines whether or not the rewind force measurement falls within a predetermined range, and initiates corrective action at the fluid infusion device when the rewind force measurement does not fall within that range. Thus, if the rewind force measurement is less than the lower threshold force (query task 208), then the fluid infusion device initiates and executes appropriate corrective action (task 210). Similarly, if the rewind force measurement is greater than the upper threshold force (query task 212), then the fluid infusion device initiates and executes appropriate corrective action (task 214). The corrective action taken by the fluid infusion device may include one or more of the following, without limitation: generating an alert or an alarm at the fluid infusion device; stopping or inhibiting fluid delivery; presenting instructions, a maintenance reminder, or a message to the user; or the like. In practice, an alert, alarm, or warning may include, without limitation: sounds; one or more synthesized voices; vibrations or other haptic feedback; displayed symbols or messages; lights; transmitted signals; Braille output; or the like. Other forms of corrective action include, without limitation: running a self test of the fluid infusion device; recalibrating the threshold forces; temporarily disabling the fluid infusion device; or the like.

A rewind force measurement that is less than the lower threshold force indicates that the measured force is less than the actual force applied to the force sensor. Consequently, it may be more difficult for the fluid infusion device to accurately and quickly detect the onset of an occlusion in the fluid path based on the force sensor output. On the other hand, a rewind force measurement that is greater than the upper threshold force indicates that the measured force is greater than the actual force applied to the force sensor. Consequently, the fluid infusion device might detect the onset of an occlusion too soon, or falsely detect an occlusion. Therefore, the type of corrective action taken at task 210 may be different than the type of corrective action taken at task 214. In this regard, different alert characteristics (colors, volume, frequency, sounds), different message content or formats, and/or different combinations of the corrective actions described above could be initiated and executed at tasks 210, 214.

It should be appreciated that the fluid infusion device processes the output levels associated with the force sensor to determine the current operating health of the force sensor. If the rewind force measurement falls within the specified range (i.e., it is greater than the lower threshold force and less than the upper threshold force), then the fluid infusion device can continue operating as usual. For example, the fluid infusion device can complete the rewind operation (task 216, which may be performed before or during tasks 206, 208, 210, 212, 214) before placement of a new fluid reservoir into the fluid infusion device. After the new fluid reservoir is installed, the process 200 activates a reservoir seating operation (task 218) and uses the force sensor to detect when the new fluid reservoir is seated in the fluid infusion device. In this regard, the drive motor assembly is activated to advance the slide until a predetermined seating force has been detected (task 220). After detection of this seating force, the drive motor assembly can be further advanced by an appropriate amount during a priming operation, which is activated to prepare the fluid infusion device and the new fluid reservoir for normal operation.

As mentioned above, a rewind operation and the related force measurements could be performed before the fluid reservoir needs to be replaced. If the process 200 determines that the force sensor is operating as expected during such a rewind operation, then task 218 and task 220 are performed to return the slide 121 to its former position in contact with the piston 144. Thereafter, fluid delivery may continue as though the rewind operation never took place.

During normal use, the fluid infusion device regulates the delivery of fluid from the fluid reservoir by controlling the movement of the drive motor assembly (task 222). The same force sensor used to determine the rewind force measurements can also be used to monitor for the onset of an occlusion (task 224). In particular, the force imparted to the force sensor (which is indicative of the pressure in the fluid reservoir) is determined and analyzed in accordance with one or more occlusion detection schemes to detect an occlusion of the infusion set or elsewhere in the fluid delivery path.

In certain embodiments, the measured rewind forces (see task 206) observed during operation are recorded in the memory of the device. The historical rewind force data may be used to detect trends and drifting in the measured rewind force, e.g., consistently decreasing, consistently increasing, random variation, or the like. Thus, even if a measured rewind force does not trigger corrective action, the rewind force values can be saved for diagnostic purposes, statistical evaluation of the device, and the like.

Figure 6:
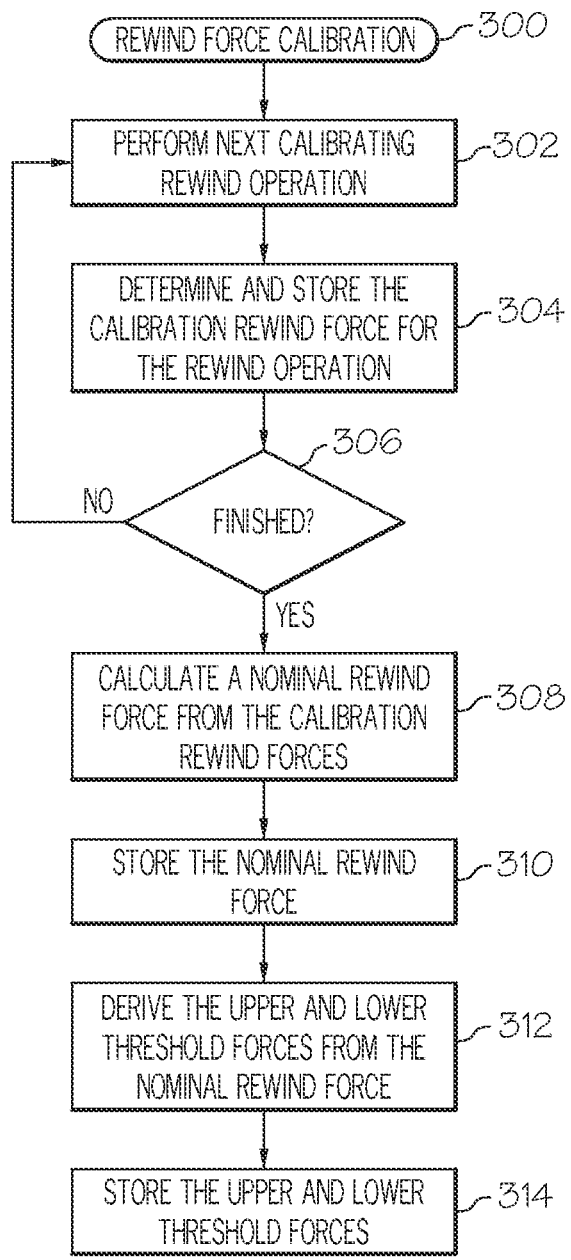
FIG. 6 is a flow chart that illustrates an embodiment of a rewind force calibration process for a fluid infusion device.

The preceding description of the process 200 illustrates how rewind force thresholds can be used to check the operating health of the force sensor. The threshold forces may be fixed or adaptive (to accommodate and compensate for drifting of the force sensor). In this regard, FIG. 6 is a flow chart that illustrates an embodiment of a rewind force calibration process 300 for a fluid infusion device, such as the fluid infusion device 100. In certain scenarios, the process 300 is performed at least once during manufacturing of the fluid infusion device, and the calibrated threshold forces are stored as fixed values for the life of the device. In other situations, the process 300 could be performed periodically (e.g., at the request of the user, every year, or in accordance with a maintenance schedule). The illustrated embodiment of the process 300 begins by performing a calibrating rewind operation (task 302). No fluid reservoir is present during calibration, and the drive motor assembly is controlled as necessary to execute a rewind operation.

During the calibrating rewind operation, the process 300 determines a calibration rewind force imparted to the force sensor (task 304). Task 304 could obtain a single rewind force measurement at any time during the calibrating rewind operation, it could calculate an average calibration rewind force based upon any number of rewind force measurements obtained during the calibrating rewind operation, or it could generate any calibration rewind force value or metric that is based upon one or more individual calibration rewind force measurements obtained during the calibrating rewind operation. For simplicity, this particular embodiment of the process 300 assumes that a single calibration rewind force measurement is determined at task 304. If the calibration period is finished (query task 306), then the process 300 continues. If not, the process 300 performs another calibrating rewind operation and determines a respective calibration rewind force measurement for that operation. In other words, tasks 302, 304, 306 can be repeated any desired number of times, resulting in a plurality of calibration rewind forces that can be saved for subsequent analysis and processing.

Upon completion of the calibration period, the process 300 calculates a nominal rewind force from the plurality of calibration rewind forces (task 308). The nominal rewind force can be determined using any desired formula, algorithm, relationship, or equation. For the simple implementation described here, the nominal rewind force is calculated as an average of the plurality of calibration rewind forces. As mentioned previously, the nominal rewind force is ideally equal or equivalent to a load of zero pounds on the drive motor assembly. Accordingly, an acceptable nominal rewind force will typically be within the range of about −0.50 to +0.50 pounds (this range is merely exemplary, and an embodiment could utilize different upper and/or lower values). In this regard, the process 300 might check the calculated nominal rewind force to ensure that it falls within a predetermined range of acceptable values. Thus, if the nominal rewind force falls outside of that range, the process 300 could generate an alarm, an alert, or a warning for the user, and/or repeat the portion of the calibration routine associated with tasks 302, 304, 306, and 308.

Assuming that the calculated nominal rewind force is acceptable, it can be stored in a memory element of the fluid infusion device (task 310) for future reference if needed. For this particular embodiment, the process 300 derives the lower threshold rewind force and the upper threshold rewind force from the calculated nominal rewind force (task 312). For example, the lower threshold force might be calculated by subtracting a designated amount from the nominal rewind force, and the upper threshold force might be calculated by adding a designated amount to the nominal rewind force. Moreover, the manner in which these threshold forces are calculated could vary as a function of the nominal rewind force itself. For instance, one threshold calculation scheme could be used when the nominal rewind force is greater than zero, and a different threshold calculation scheme could be used when the nominal rewind force is less than zero. After the rewind force thresholds have been derived, they can be stored in a memory element of the fluid infusion device (task 314) for subsequent use as needed, e.g., during execution of the process 200. In practice, these rewind force thresholds can be saved as fixed values that do not change during the operating life of the fluid infusion device. In this manner, the process 300 results in a specified range of rewind forces that is indicative of a healthy operating status of the force sensor.

In accordance with another approach, the operating health of the force sensor 126 is checked more frequently, namely, at times other than during a rewind operation. This alternate approach (which may be utilized in conjunction with the first approach described above) checks the health of the force sensor in an ongoing manner without having to wait until a rewind operation. More particularly, this technique checks the measured or detected force associated with the drive motor assembly at designated motor pulses (e.g., at every motor pulse). If the measured force is below a predetermined value, the fluid infusion device will take corrective action because this condition indicates that the force sensor has drifted beyond its limit in the negative direction. If the measured force is above a predetermined value, then the fluid infusion device assumes that the force sensor has drifted in the positive direction, which might result in false or early detection of an occlusion.

Figure 7:
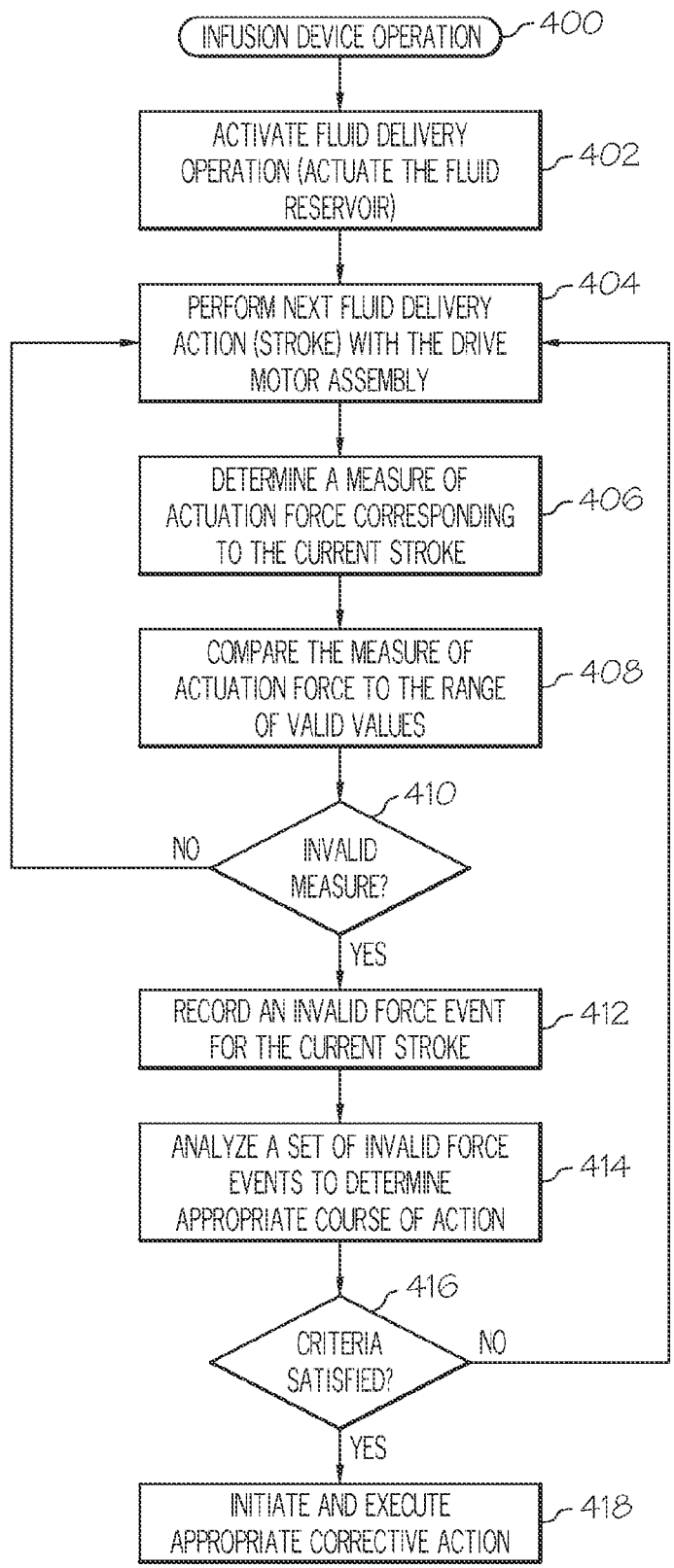
FIG. 7 is a flow chart that illustrates another embodiment of a process associated with the operation of a fluid infusion device.

FIG. 7 is a flow chart that illustrates another embodiment of a process 400 associated with the operation of a fluid infusion device, such as the fluid infusion device 100 described above. The process 400 may begin any time after activating a fluid delivery operation of the fluid infusion device (task 402). During a fluid delivery operation, the drive motor assembly is used to actuate the fluid reservoir in a controlled manner. In certain implementations, fluid delivery operations are carried out in a stepwise manner such that fluid is administered in discrete fluid delivery strokes (or pulses) of the slide. In practice, a fluid delivery operation may involve multiple fluid delivery strokes; the exact number will depend on the desired amount of fluid to be delivered. Accordingly, the process 400 continues by performing the next fluid delivery action, pulse, or stroke with the drive motor assembly (task 404), and determining and saving the corresponding measure of actuation force imparted to the force sensor during that fluid delivery action (task 406).

Next, the process 400 compares the measure of actuation force to a range of valid values for the fluid infusion device (task 408). In practice, there will be a range of force sensor outputs or readings that correspond to or otherwise represent normally expected measures of actuation forces. For example, if the force sensor is operating as expected, then it might have a limited and predetermined analog output range, which in turn corresponds to a limited and predetermined range of encoded digital values. If, however, the force sensor is damaged, is beginning to fail, or is otherwise operating in an unexpected or unusual manner, then the resulting analog output and encoded digital values could be outside of the normally expected range. Measured values of actuation force that are outside of the normally expected range are therefore treated as invalid or undefined measures.

If the current measure of actuation force is not invalid as defined by the particular settings and configuration of the fluid infusion device (query task 410), then the process 400 may return to task 404 to perform the next fluid delivery action. This enables the fluid infusion device to monitor the operating integrity of the force sensor during fluid delivery and in an ongoing and dynamic manner. If, however, the current measure of actuation force is outside the range of valid values, then the process may generate a flag or otherwise record an invalid force event for the current measure of actuation force (task 412). The recorded event may include information such as, for example, the delivery time of the current stroke, the current measure of actuation force, the current position of the slide or drive motor, or the like. Data associated with the recorded event can be saved for subsequent analysis, for reporting purposes, for troubleshooting or diagnostic purposes, etc. For instance, this embodiment of the process 400 continues by analyzing a set of invalid force events to determine a course of action for the fluid infusion device (task 414). In this regard, the set of invalid force events may represent a designated number of past invalid force events, including the current invalid force event, collected over a particular period of time, collected for a designated number of delivery strokes, or the like. In certain situations, the set of invalid force events may correspond to only one event, which could be sufficient to trigger an alarm or an alert if deemed necessary. This allows the process 400 to initiate corrective action based on a single actuation stroke or pulse, based on an average measure of multiple pulses, based on detected patterns of measured forces, or the like. Task 414 may be performed to reduce the likelihood of false alerts or false alarms associated with the operating health of the force sensor. In this regard, the process 400 may be used to detect a positive drift and/or a negative drift in the force sensor, which may result in the lack of timely alerts. Thus, the detection of only one invalid force event during an extended period of time or over the course of many delivery strokes can be disregarded without triggering an alert.

The process 400 could utilize any type of criteria that influences whether or not a single invalid force event or a set of invalid force events will cause the fluid infusion device to respond. For example, the criteria may dictate that at least a threshold number of invalid force events corresponding to consecutive fluid delivery actions must be recorded before a user alert is generated. As another example, the criteria may dictate that at least a threshold number of invalid force events must be recorded within a designated period of time (such as 60 minutes) before any corrective action is taken. The criteria may be chosen such that transient conditions that might influence the operation of the force sensor (e.g., handling of the device, bumping or dropping the device, driving over a pothole, etc.) do not trigger an alarm. Rather, the criteria may be selected such that the fluid infusion device is given the opportunity to recover and settle from such transient events.

Accordingly, if certain designated criteria is satisfied (query task 416), then the process 400 can initiate and execute appropriate corrective action at the fluid infusion device (task 418). If the criteria has not been satisfied, then the process 400 may return to task 404 to perform the next fluid delivery action. Thus, some form of corrective or remedial action can be taken in response to the recording of one or more invalid force events, where the recorded events are indicative of poor operating health of the force sensor.

Task 418 may initiate and execute any of the corrective actions described above for tasks 210 and 214 of the process 200.

The process 400 represents a simplified embodiment that analyzes actuation forces and checks for valid measures of actuation force from one delivery stroke or pulse of the drive motor assembly to another. Alternative embodiments, however, could implement a more complex scheme that calculates and considers any suitable parameter, measure of force, force-related metric, or the like. For example, rather than compare the actuation forces to a range of valid measures per se, the fluid infusion device could instead calculate any appropriate parameter from the measured actuation force, where the parameter is somehow indicative of the operating health of the force sensor, and then compare the value of that parameter to certain predetermined performance criterion for the force sensor. If the parameter does not satisfy the performance criterion, then the fluid infusion device can take corrective or remedial action.

In some embodiments, the fluid infusion device 100 is suitably configured to check the operating condition of the force sensor 126 using a known and calibrated force applied to the force sensor 126. Although not always required, this example assumes that the force sensor 126 is tested after removing the fluid reservoir 111 and during a time when fluid need not be dispensed. Imparting a known nonzero calibration force to the force sensor 126 can be accomplished using any suitable component, device, fixture, or equipment. In accordance with one exemplary embodiment, the fitting 110 is replaced with a calibration fitting that is provided with a precisely calibrated spring or other element that provides a known force at a specified amount of deflection. After installing the calibration fitting, the slide 121 is advanced by a designated amount, which can be controlled by monitoring encoder counts or other metrics related to the operation of the drive motor 136. When the slide 121 has advanced by the designated amount, the force element (e.g., the spring) is expected to impart the calibrating force to the slide 121, which in turn imparts the calibrating force to the force sensor 126.

When the slide 121 has reached the calibration position, the corresponding measure of actuation force is recorded and compared to a value associated with the expected calibrating force. If the recorded value is different than the expected calibration value by more than a stated amount, then the fluid infusion device 100 (and/or the user) can assume that the force sensor 126 is defective or otherwise not functioning according to specification. It should be appreciated that the calibration force should fall within the normal measuring range of the force sensor 126.

Reservoir Seating (Presence) Monitoring

The force sensor 126 in the fluid infusion device 100 may also be utilized to monitor the presence and seating status of the fluid reservoir 111. In this regard, the electronics module 162 of the fluid infusion device 100 can be utilized to process the output levels of the force sensor 126 to determine the seating status of the fluid reservoir 111 in the reservoir cavity 134 in an ongoing manner. The fluid infusion device 100 can alert the user when the fluid reservoir 111 has been accidentally removed or inadvertently dislodged. The fitting 110 might be inadvertently rotated or loosened during physical activity (e.g., while the user is playing a sport or exercising), which in turn might result in removal or dislodging of the fluid reservoir 111. When this happens, proper coupling between the piston 144 of the fluid reservoir 111 and the coupler 142 of the slide 121 could be lost. For safe measure, the fluid infusion device 100 notifies the user shortly after the fluid reservoir 111 is partially removed, completely removed, or dislodged by more than a predetermined amount.

The fluid infusion device 100 uses the force sensor 126 to determine the seating status of the fluid reservoir 111. Accordingly, no additional components, sensors, or assembly time is needed to implement this feature. In certain embodiments, the fluid infusion device 100 uses a scheme that adaptively tracks the forces of delivery strokes. The fluid infusion device 100 records the force of a delivery stroke. If the measured force remains the same or increases from stroke-to-stroke, then the fluid infusion device 100 assumes that a fluid reservoir is in place and is properly seated. Moreover, slight variations in the detected force can be disregarded to contemplate normal and expected force variations that typically occur along the travel path of a fluid reservoir. However, a characterized drop in force that is greater than a certain amount indicates that (1) the fluid reservoir 111 has been removed or dislodged or (2) the fluid infusion device 100 may have been dropped or bumped, temporarily disturbing the force sensor 126. For the second scenario, design engineers can characterize how many pulses (delivery strokes) and/or how much time is typically needed to allow the fluid infusion device 100 to recover from a disturbing impact or force, assuming that the fluid reservoir 111 remains present and properly seated. If the measured force does not return to a nominal value after a designated number of strokes or a predetermined amount of time, the fluid infusion device 100 can conclude that the fluid reservoir 111 has been removed or disturbed and, in turn, generate an alert or a warning message for the user.

Notably, the reservoir presence scheme is adaptive in nature, and it takes into account variations such as sensor drift, reservoir frictional force variation, and minor shocks. The reservoir presence methodology actively monitors for an ongoing drop in force greater than a set value. This approach is desirable because it accommodates variations (such as sensor drift) that might be introduced over the life of the fluid infusion device 100, variations from one reservoir to another, and variations (such as fluid pressure) that might occur during use of a single reservoir. For example, if frictional force increases due to reservoir dynamics, the fluid infusion device 100 will adapt and set the increased force measure as a new baseline value. Similarly, if the frictional force is decreasing due to reservoir dynamics, the fluid infusion device 100 will adapt the lower force measure as the new baseline value (as long as the rate of decrease and/or the force variation is less than a specified amount). This feature accommodates variation in frictional force without false alarms. Accordingly, the fluid infusion device 100 adaptively resets the baseline force value as long as the rates of change are within normal limits.

Figure 8:
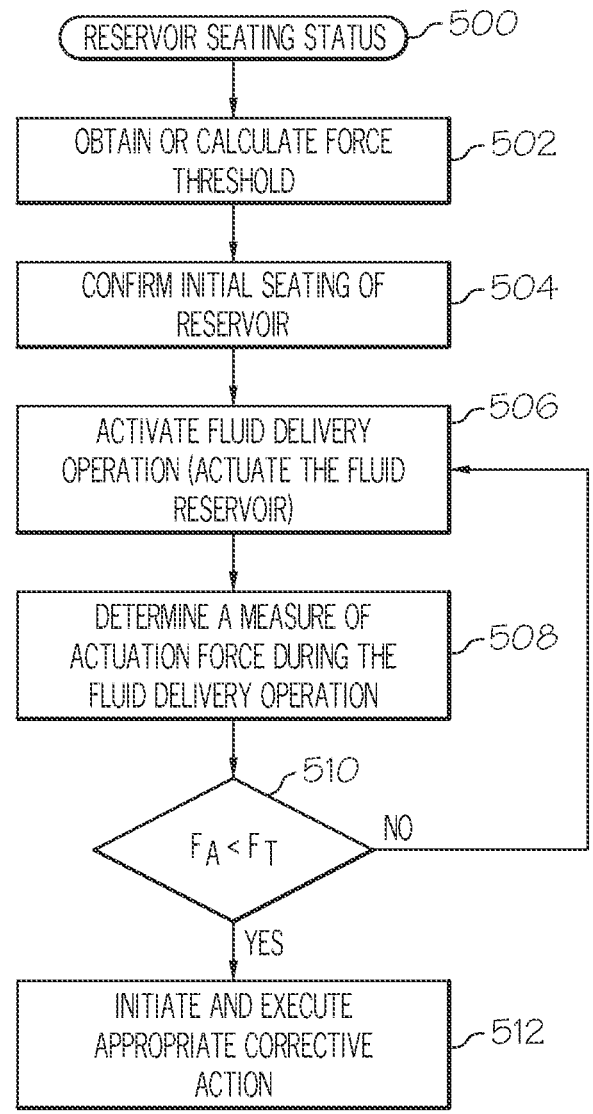
FIG. 8 is a flow chart that illustrates an embodiment of a process that checks the seating status of a fluid reservoir of a fluid infusion device.

FIG. 8 is a flow chart that illustrates an embodiment of a process 500 that checks the seating status of a fluid reservoir of a fluid infusion device, such as the fluid infusion device 100 described above. The process 500 employs a simple force threshold for purposes of determining the seating status of the fluid reservoir. In this regard, the process 500 may begin by obtaining, calculating, or accessing the force threshold (task 502), which represents an amount of force that is indicative of a dislodged, removed, displaced, or otherwise unseated state of the fluid reservoir. The force threshold may be adaptively updated in response to certain operating conditions, it may be one of a plurality of different available threshold values, it may be a predetermined and fixed value, or the like. For this example, the force threshold is a pre-stored value that is fixed during the operating lifespan of the fluid infusion device. In other embodiments (described below), the force threshold can be calculated in a dynamic manner to contemplate typical variations such as drifting of the force sensor.

Under typical operating conditions for exemplary embodiments, the normally expected force imparted to the force sensor when the fluid reservoir is properly seated is less than about 1.5 pounds. Moreover, under typical operating conditions for exemplary embodiments, the normally expected actuation force imparted to the force sensor during a fluid delivery stroke is less than about 1.5 pounds. In certain implementations, the force threshold used by the process 500 is calculated as a function of the nominal seating force and/or as a function of the nominal actuation force, and the force threshold is stored in a memory element of the fluid infusion device. For example, the force threshold might be calculated to be less than the average fluid delivery actuation force by a given amount, such as a percentage of the average fluid delivery actuation force. As another example, the force threshold is calculated such that it is a predefined amount of force less than the nominal expected actuation force. In practice, regardless of the manner in which it is calculated, the force threshold will typically be less than about 0.5 pounds.

In practice, the process 500 can be initiated whenever a fluid reservoir is installed into the fluid infusion device. Accordingly, the process 500 may confirm the initial seating of the fluid reservoir in the reservoir cavity (task 504). Task 504 may additionally (or alternatively) confirm when the fluid infusion device has performed a priming operation, which typically occurs after installation of a fluid reservoir. After confirming that the fluid reservoir has been properly seated and/or otherwise properly installed, the fluid infusion device will eventually activate a fluid delivery operation, which in turn actuates the fluid reservoir with the drive motor assembly (task 506). As described in more detail above, actuation of the fluid reservoir causes an amount of force to be imparted to the force sensor. Accordingly, the process 500 determines a measure of actuation force imparted to the force sensor during the fluid delivery operation (task 508). Task 508 could obtain a single actuation force measurement at any time during the fluid delivery operation, it could calculate an average actuation force based upon any number of actuation force measurements obtained during the fluid delivery operation (e.g., a plurality of actuation forces corresponding to a plurality of consecutive delivery strokes), or it could generate any actuation force value or metric that is based upon one or more individual actuation force measurements obtained during the fluid delivery operation. For simplicity, this particular embodiment of the process 500 assumes that a single actuation force measurement is determined at task 508. For this example, task 508 determines the measure of actuation force during the fluid delivery stroke itself. Alternatively (or additionally), task 508 could determine the measure of actuation force between fluid delivery strokes, and/or after a final fluid delivery stroke.

The process 500 may continue by comparing the actuation force measurement to one or more threshold forces. For this example, the process 500 compares the measure of actuation force to an amount of force (i.e., the force threshold obtained at task 502) that is less than the normally expected actuation forces of the fluid infusion device. Accordingly, the process 500 checks whether or not the measure of actuation force ($F_A$) is less than the force threshold ($F_T$) at query task 510. If the measure of actuation force is not less than the force threshold, then the process 500 assumes that the fluid reservoir is still in place and remains properly seated. Accordingly, the process 500 returns to task 506 to continue monitoring actuation force for the current fluid delivery operation (and for subsequent fluid delivery operations). If, however, query task 510 determines that the measure of actuation force is less than the force threshold and, therefore, that the measure of actuation force is indicative of an unseated state, then the fluid infusion device initiates and executes appropriate corrective action (task 512). The corrective action taken by the fluid infusion device may include, without limitation, one or more of the actions described above for the process 200 (see FIG. 5). It should be appreciated that the process 500 may consider any number of events (i.e., determinations that the measure of actuation force is less than the force threshold) and analyze a set of events to determine whether or not to initiate the corrective action. In this regard, the process 500 may determine whether a set of events satisfies certain predetermined criteria before taking corrective action, as described above with reference to tasks 412, 414, and 416 of the process 400.

Figure 9:
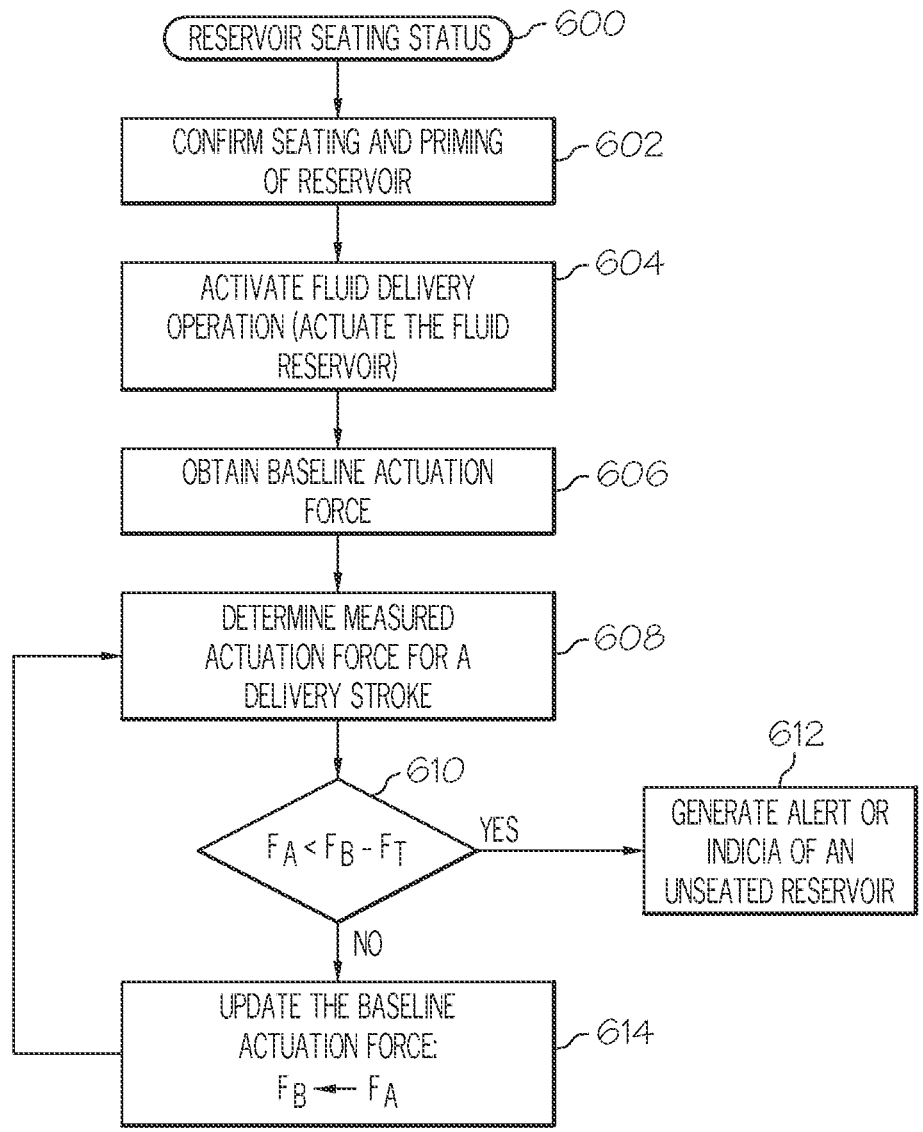
FIG. 9 is a flow chart that illustrates another embodiment of a process that checks the seating status of a fluid reservoir of a fluid infusion device.

The process 500 is one exemplary embodiment that utilizes a fixed force threshold value to determine whether or not the fluid reservoir is seated. In contrast, FIG. 9 is a flow chart that illustrates another embodiment of a process 600 that employs an adaptive scheme for checking the seating status of the fluid reservoir. The process 600 can be performed whenever a fluid reservoir is installed into the fluid infusion device. Thus, the process 600 may begin by confirming the initial seating and priming of the fluid reservoir (task 602), and activating a fluid delivery operation (task 604), as described above for the process 500. After initial seating of the fluid reservoir, the process obtains a baseline actuation force imparted to the force sensor (task 606). The baseline actuation force may correspond to a measure of actuation force that is obtained during the priming operation or shortly thereafter, or it may correspond to a measure of actuation force that is obtained during the first fluid delivery operation for a new fluid reservoir. The process 600 assumes that the baseline actuation force is measured while the fluid reservoir is properly seated. Accordingly, the baseline actuation force can be stored in a memory element of the fluid infusion device for later use.

Eventually, the process 600 determines a measured actuation force imparted to the force sensor, where the measured actuation force corresponds to a designated delivery stroke of the drive motor assembly (task 608). Task 608 could obtain a single actuation force measurement at any time during the fluid delivery operation, it could calculate an average actuation force based upon any number of actuation force measurements obtained during the fluid delivery operation (e.g., a plurality of actuation forces corresponding to a plurality of consecutive delivery strokes), or it could generate any actuation force value or metric that is based upon one or more individual actuation force measurements obtained during the fluid delivery operation. For simplicity, this particular embodiment of the process 600 assumes that a single actuation force measurement is determined at task 608. As mentioned previously, the actuation force could be determined during the fluid delivery stroke itself, between fluid delivery strokes, or after a final fluid delivery stroke.

The process 600 may continue by comparing the actuation force measurement to a measure of force that is influenced by the baseline actuation force ($F_B$). For this example, the process 600 checks (query task 610) whether the measured actuation force ($F_A$) is less than the baseline actuation force by some predetermined amount ($F_T$), which may be a fixed, adaptive, or dynamic threshold, as explained above for the process 500. In other words, query task 610 determines whether $F_A < F_B - F_T$. If query task 610 determines that the measure of actuation force is indicative of an unseated or dislodged fluid reservoir, then the fluid infusion device initiates and executes appropriate corrective action (task 612), e.g., generates an alert or some indicia of an unseated fluid reservoir. Alternatively or additionally, the corrective action taken by the fluid infusion device may include, without limitation, one or more of the actions described above for the process 200 (see FIG. 5). It should be appreciated that the process 600 may consider any number of events (i.e., individual determinations that $F_A < F_B - F_T$) and analyze a set of events to determine whether or not to initiate the corrective action. In this regard, the process 600 may determine whether a set of events satisfies certain predetermined criteria before performing task 612 (see the above description of tasks 412, 414, and 416 of the process 400).

If the measure of actuation force is indicative of a properly seated fluid reservoir, then the process 600 updates the baseline actuation force as a function of the measured actuation force (task 614). For this particular embodiment, task 614 updates the baseline actuation force by saving the measured actuation force for use as the next baseline actuation force. In practice, the fluid infusion device could implement a maximum and/or a minimum allowable baseline actuation force to ensure that the process 600 maintains a realistic baseline value. If for some reason the measured actuation force falls outside of the stated range of baseline force values, the fluid infusion device could generate an alert or take appropriate action. In this regard, a maximum or minimum value could serve as a confirmation or check of the operating health of the force sensor (see the Sensor Health Monitoring section of this description). Referring back to task 614, after updating the baseline actuation force, the process 600 returns to task 708 to continue monitoring actuation force for the current fluid delivery operation (and for subsequent fluid delivery operations). Thus, the baseline actuation force is adjusted and updated in an ongoing manner while the process 600 monitors the seating status of the fluid reservoir. This adaptive approach enables the process 600 to consider and compensate for slight variations in measured actuation forces.

Figure 10:
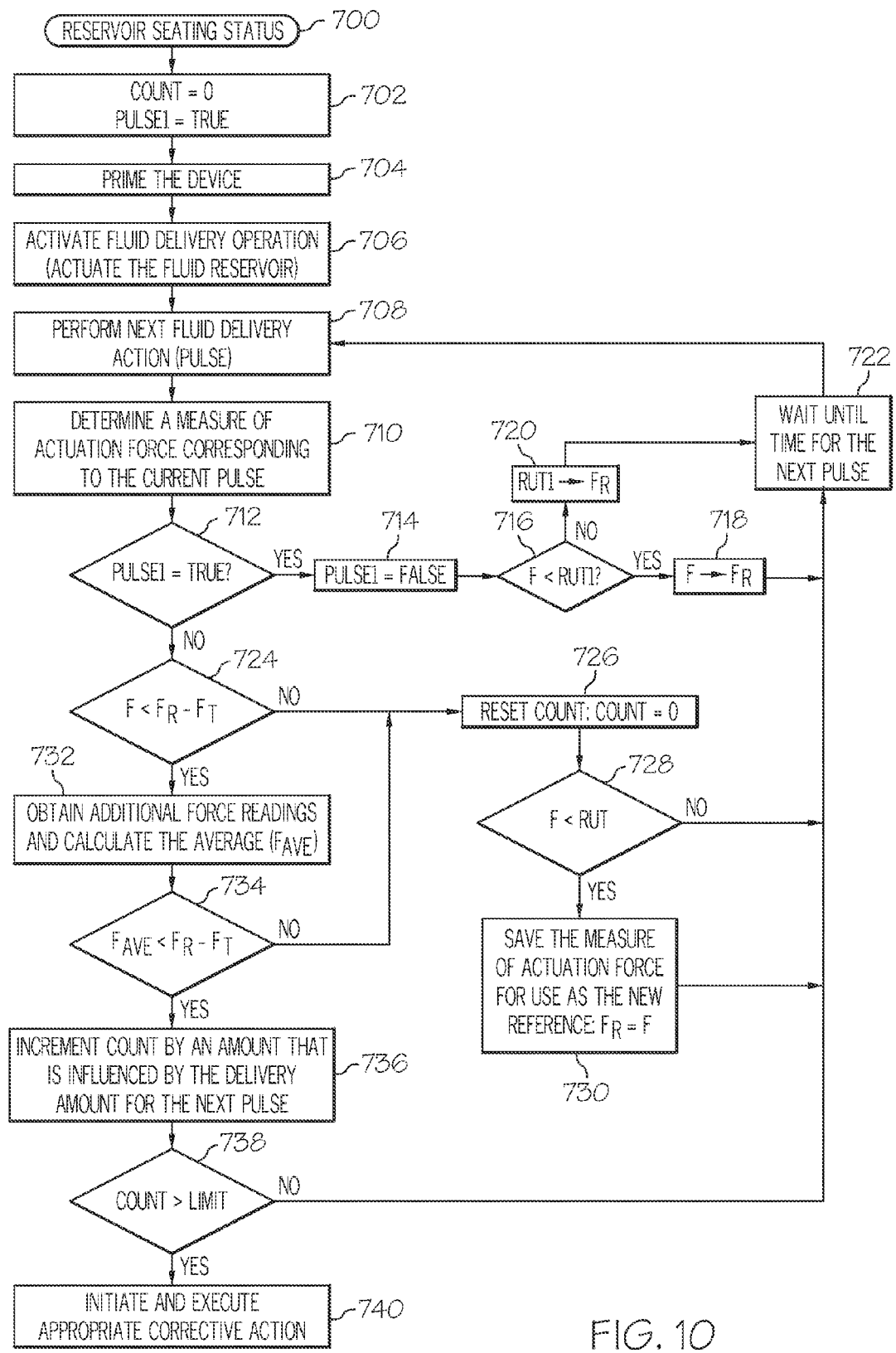
FIG. 10 is a flow chart that illustrates yet another embodiment of a process that checks the seating status of a fluid reservoir of a fluid infusion device.

FIG. 10 is a flow chart that illustrates yet another embodiment of a process 700 that checks the seating status of a fluid reservoir. The process 700 uses a threshold force value that corresponds to the maximum expected variation in actuation force for the fluid reservoir. This threshold force value may be empirically determined, calculated based on known operating parameters of the fluid infusion device, or generated and dynamically updated during operation of the fluid infusion device. In certain embodiments, the threshold force value is determined and stored as a fixed value during the operating lifespan of the fluid infusion device. For example, and without limitation, the typical fluid delivery force for a fluid reservoir might be about 1.4 pounds between initial piston seating and depletion of the fluid reservoir, and the threshold force value might be about 0.2 pounds.

The process 700 obtains the measures of actuation force imparted to the force sensor for consecutive fluid delivery pulses (in practice, a measure of actuation force is recorded for each fluid delivery pulse). The process 700 calculates a pulse-to-pulse difference between consecutive fluid delivery pulses, where the pulse-to-pulse difference is based on respective measures of actuation force for the consecutive fluid delivery pulses. If the pulse-to-pulse difference is greater than the designated threshold force value, then the fluid infusion device initiates corrective action in some manner. In other words, if the difference in actuation force between the last fluid delivery pulse and the current fluid delivery pulse is more than the normally expected force variation, then the fluid infusion device assumes that the detected condition is indicative of a dislodged or removed fluid reservoir, or a transient state caused by an impact or sudden acceleration to the fluid infusion device. Note that in order to assume a removed or dislodged reservoir, the difference in force from one pulse to the next must be negative, i.e., the measured force has decreased rather than increased.

The process 700 may include some tasks that are similar or identical to counterpart tasks found in the process 600, and such tasks will not be redundantly described here. The process 700 assumes that the fluid reservoir has already been properly seated for fluid delivery. This embodiment of the process 700 begins by initializing and maintaining a count (task 702) that is indicative of the seating status of the fluid reservoir. The count may be initialized at any suitable value, although this example assumes that the count is initialized at a value of zero. The process 700 also sets the value of PULSE1 to "True" (task 702). The value of PULSE1 is True only for the first actuation pulse following installation of a fluid reservoir. For all subsequent delivery pulses, the value of PULSE1 is False. The fluid infusion device is primed (task 704) such that fluid is introduced into the fluid pathway and through the infusion set tubing. During priming, the force imparted to the force sensor typically spikes (to about 1.4 pounds) when the slide initially contacts the plunger of the reservoir. After priming, however, the force decays and settles to a lower value (typically around 0.5 pounds).

The process 700 activates a fluid delivery operation (task 706) to actuate the fluid reservoir, and performs the next fluid delivery action, stroke, or pulse (task 708). As explained in more detail below, tasks 706 and 708 are usually performed after the priming operation is complete and after the force has settled to its nominal value (of about 0.5 pounds). If, however, the user commands a fluid delivery operation prematurely while the force is still decaying, then the force imparted to the force sensor at that time may be above the nominal value. The process 700 contemplates this scenario, as described below.

The process 700 continues by determining or obtaining a current measure of actuation force imparted to the force sensor for the current fluid delivery pulse (task 710), as described previously. The current measure of actuation force (F) is recorded or saved in an appropriate manner. If PULSE1 is True (query task 712), meaning that the pulse actuated at task 708 is the first pulse for the installed reservoir, then the process 700 continues by setting the value of PULSE1 to "False" (task 714), and by comparing the current measure of actuation force (F) to a reference upper threshold force value that applies to initial pulses (RUT1), as indicated by query task 716. The value of RUT1 is selected to account for situations where the initial pulse is commanded prematurely, i.e., before the force has settled to its nominal value after priming. In other words, RUT1 is selected to contemplate the possibility of unusually high force measurements associated with the first pulse commanded for a newly installed reservoir. For this particular example (where the normally expected nominal actuation force for the fluid reservoir is about 0.4 pounds), the value of RUT1 may be chosen to be about 0.5 pounds, without limitation.

If the current measure of actuation force is less than RUT1 (query task 716), then the process 700 stores the current measure of actuation force (task 718) for use as an adaptive reference force value ($F_R$), which is used for comparison purposes against subsequent force measurements. Execution of task 718 indicates that the actuation force associated with the initial delivery pulse does not represent a force measured shortly after priming, while the fluid in the delivery path is still settling to its nominal state. On the other hand, if the current measure of actuation force (F) is not less than RUT1 (query task 716), then the process 700 stores the value of RUT1 as the current value of $F_R$ (task 720). Execution of task 720 indicates that the actuation force associated with the initial delivery pulse may have been sampled during a time when the fluid in the delivery path is still settling and, therefore, the measured force is still decaying from the relatively high value (e.g., about 1.4 pounds). Consequently, under this scenario the process 700 uses RUT1 as the current adaptive reference force value.

After the value of $F_R$ has been set (task 718 or task 720), the process 700 waits for the next fluid delivery pulse (task 722). When it is time to perform the next fluid delivery pulse, the process 700 returns to task 708 and continues as described above. In contrast to that described above, however, the value of PULSE1 is False for the second and all further delivery pulses. Referring again to query task 712, if PULSE1 is not True (i.e., PULSE1=False), then the process 700 may continue by comparing the current measure of actuation force to the difference between the adaptive reference force value ($F_R$) and a threshold force value (query task 724). For this example, the adaptive reference force value ($F_R$) may correspond to a past measure of actuation force that was recorded for a previous fluid delivery pulse, or it may correspond to RUT1, as described above. In particular embodiments, $F_R$ might represent the measure of actuation force for the immediately preceding fluid delivery pulse (indeed, under normal operating conditions where the fluid reservoir remains properly seated, $F_R$ will be adaptively updated to reflect the most recent measure of actuation force). In other words, the previous fluid delivery pulse associated with $F_R$ and the current fluid delivery pulse will typically be consecutive fluid delivery pulses. Thus, the process 700 stores, maintains, and updates the adaptive reference force value as needed during operation of the fluid delivery device.

In practice, the process 700 might generate or store an initial value of $F_R$ whenever a new fluid reservoir is installed, at the beginning of a fluid delivery operation, at designated times, at the request of the user, or at other appropriate times. This example assumes that $F_R$ is initialized as described above in response to the first fluid delivery pulse of a fluid delivery operation. Thus, under typical and normal operating conditions the first measure of actuation force will be used as $F_R$ for the immediately following fluid delivery pulse. If, however, the first measure of actuation force exceeds the initial upper threshold value, then the initial upper threshold value RUT1 will instead be used as $F_R$ for the next fluid delivery pulse.

Referring again to query task 724, if the current measure of actuation force (F) is not less than the difference between the adaptive reference force value ($F_R$) and the threshold force value ($F_T$), then the process 700 assumes that the fluid reservoir remains properly seated. Accordingly, the process 700 resets the count to its initial value, e.g., zero (task 726). The illustrated embodiment of the process 700 continues by comparing the current measure of actuation force (F) to an upper threshold force value (RUT), as indicated by query task 728. This upper threshold value is selected such that it is indicative of the expected maximum actuation force for the fluid reservoir. For this particular example (where the normally expected actuation force for the fluid reservoir is about 1.4 pounds), the upper threshold force value may be chosen to be about 1.8 pounds, without limitation. If the current measure of actuation force is less than the upper threshold force value, the process 700 stores the current measure of actuation force for use as $F_R$ with the next iteration (task 730). In this regard, $F_R$ can be adaptively and dynamically updated in an ongoing manner during the fluid delivery operation. After updating $F_R$, the process 700 waits until it is time to perform the next fluid delivery pulse (task 722). Referring back to query task 728, if the current measure of actuation force is not less than the upper threshold force value, then the process 700 leaves $F_R$ unchanged and waits for the next fluid delivery pulse (task 722). In other words, the previous value of $F_R$ is retained for the next processing iteration. When it is time to perform the next fluid delivery pulse, the process 700 returns to task 708 and continues as described above.

Referring again to query task 724, if $F<F_R-F_T$, then the process 700 initiates some form of corrective action, which is triggered by the detection of an abnormal or unexpected measure of actuation force. In this regard, the process 700 may place the fluid infusion device into a flagged state, perform additional checks, and/or perform additional data analysis to determine whether or not to execute corrective action, issue an alert, sound an alarm, generate a user message, etc. This particular example continues by obtaining one or more additional force readings (task 732) and calculating an average measure of actuation force ($F_{AVE}$) based on the additional force readings. In practice, $F_{AVE}$ may be calculated from the current measure of actuation force and any or all of the additional force readings. In certain embodiments, task 732 collects four additional force readings, and $F_{AVE}$ is calculated as a weighted average of the current measure of actuation force and the four repeated measures of actuation force imparted to the force sensor.

Although the process 700 could use the current measure of actuation force itself as a trigger value, the illustrated embodiment instead uses $F_{AVE}$ as the trigger value. In other words, the process 700 checks whether $F_{AVE}<F_R-F_T$ (query task 734). If $F_{AVE}$ is not less than the difference between the adaptive reference force value ($F_R$) and the threshold force value ($F_T$), then the process 700 assumes that the fluid reservoir remains properly seated, resets the count to its initial value (task 726), and continues from task 726 as described above. If, however, $F_{AVE}<F_R-F_T$, then the process 700 changes the count by a designated amount to obtain an updated count (task 736). Depending upon the embodiment and the initial count value, task 736 may increase or decrease the count. In certain embodiments, task 736 changes the count by an amount that is influenced or dictated by a volume of fluid to be delivered by a subsequent fluid delivery pulse, e.g., the next fluid delivery pulse. Alternatively, task 736 might change the count by an amount that is influenced or dictated by a volume of fluid delivered by the current fluid delivery pulse, or by a previous fluid delivery pulse. In accordance with one non-limiting example, task 736 increases the count by one when the next fluid delivery pulse corresponds to a relatively low volume of fluid (e.g., 0.025 units), increases the count by two when the next fluid delivery pulse corresponds to a relatively intermediate volume of fluid (e.g., 0.050 units), and increases the count by six when the next fluid delivery pulse corresponds to a relatively high volume of fluid (e.g., 0.200 units).

The above methodology for task 736 accounts for "slack" that is created in the drive system when the fluid infusion device is dropped or when the reservoir is dislodged. For example, assume that the slack represents a separation between the plunger of the reservoir and the tip of the actuating slide, and assume that it takes six pulses (each corresponding to a delivery of 0.025 Units), equivalent to 0.15 Units, to remove the slack. Therefore, the counter limit or threshold will be set to six. If after six "counts" the slack is not removed, i.e., the force is still low, the process 700 will trigger an alarm. If the device delivers fluid in 0.025 Unit pulses, it will take six pulses and, therefore, the count is incremented by one. On the other hand, if the fluid delivery is in 0.05 Unit increments, then the counter is incremented by two; if the fluid delivery is in 0.2 Unit pulses, the counter increments by six. Accordingly, the limit or threshold is met after six 0.025 Unit pulses, after three 0.05 Unit pulses, or after only one 0.2 Unit pulse. This allows the fluid infusion device to deliver various pulses and increment correctly.

After obtaining the updated count, the process 700 checks whether the updated count satisfies certain predetermined alert criteria (query task 738). The alert criteria for the illustrated embodiment is simply a threshold count value or a limit, such as twelve or any appropriate number. Thus, if the updated count is greater than the limit, then the process 700 assumes that the fluid reservoir has been dislodged, loosened, or unseated. Consequently, the process 700 initiates and executes appropriate corrective action (task 740), e.g., generates a seating status alert or some indicia of an unseated fluid reservoir. Alternatively or additionally, the corrective action taken by the fluid infusion device may include, without limitation, one or more of the actions described above for the process 200 (see FIG. 5). If, however, query task 738 determines that the updated count does not satisfy the stated alert criteria, then the process 700 does not actually implement or execute any corrective action at this time. Rather, the process 700 may lead back to task 722 to wait for the next fluid delivery pulse, as described above. Notably, corrective action is executed by the illustrated embodiment of the process 700 only when the count exceeds the threshold limit. Moreover, the manner in which the count is reset by the process 700 ensures that unexpectedly low actuation force readings must be recorded for consecutive fluid delivery pulses before the fluid delivery device actually issues a warning or an alert. These aspects of the process 700 reduce nuisance alerts and allow the fluid infusion device to recover from transient conditions that might cause a temporary drop in the measured actuation force (e.g., dropping or bumping the fluid infusion device, mishandling the fluid infusion device, or the like). In certain embodiments, if at any point when the force is low and the count is being updated the force increases (i.e., the slide contacts the plunger of the reservoir), the counter is again reset to zero.

Figure 11:
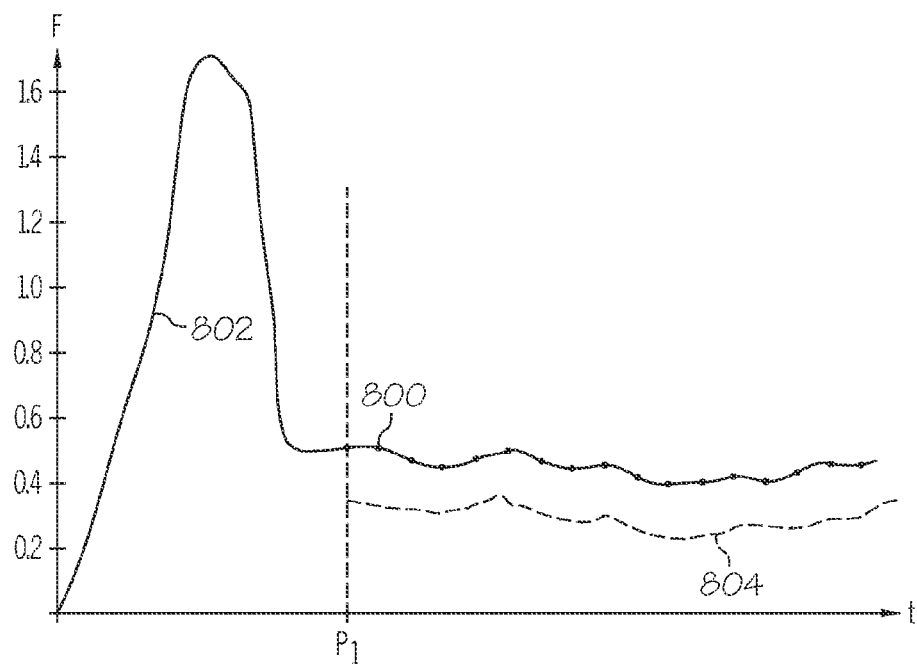
FIG. 11 is a graph that illustrates measures of actuation forces for a properly seated fluid reservoir.

FIG. 11 is a graph that illustrates measures of actuation forces for a properly seated fluid reservoir. The plot 800 represents actuation force versus time (or, equivalently, fluid delivery pulses). The initial portion 802 of the plot 800 corresponds to the seating of the fluid reservoir. In practice, the device stops the seating process when a force of about 1.4 pounds is reached. Momentum of the motor results in some additional actuation, resulting in a peak of about 1.8 pounds. After seating and priming, however, the nominal force typically settles to about 0.5 pounds. Accordingly, the label $P_1$ represents the first fluid delivery pulse following the seating/priming procedure. The dashed line 804 schematically represents the threshold force value corresponding to the allowable drop in actuation force over any two consecutive fluid delivery pulses. Notably, even though the plot 800 fluctuates somewhat, the actuation force values do not violate the limit defined by the threshold force value. In other words, the plot 800 is indicative of a properly seated fluid reservoir under normal and expected operating conditions.

Figure 12:
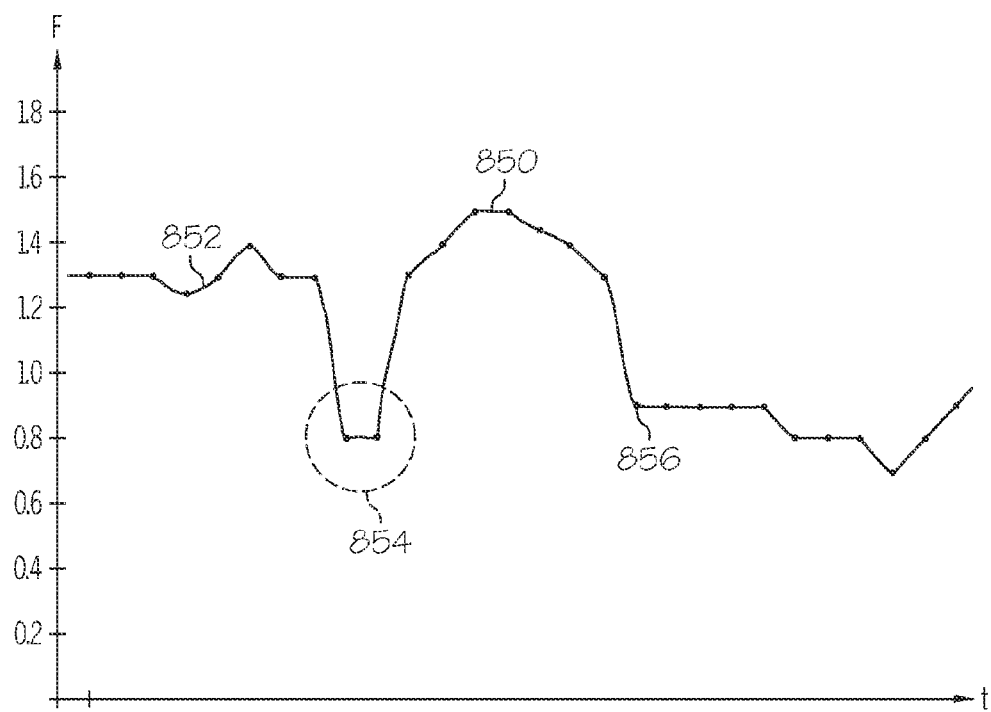
FIG. 12 is a graph that illustrates measures of actuation forces for a fluid reservoir that becomes unseated.

In contrast, FIG. 12 is a graph that illustrates measures of actuation forces for a fluid reservoir that becomes unseated. The plot 850 begins at a point after initial seating of the fluid reservoir. The initial segment 852 of the plot 850 is indicative of a properly seated fluid reservoir (assuming that the threshold force value is 0.15 pounds). The plot 850 experiences a temporary drop 854 that spans two fluid delivery pulses. For this example, the temporary drop 854 would trigger the counting mechanism described above with reference to the process 700. However, the plot 850 recovers after the temporary drop 854 and, therefore, the count would be reset and no alert would be generated. At the fluid delivery pulse 856, the plot 850 exhibits a significant and "permanent" drop. At this point, the counting mechanism would be activated. Notably, the drop in measured actuation force does not recover even after ten consecutive fluid delivery pulses. Consequently, the count continues to increase and, for this example, the upper count limit is eventually reached. At that time, the fluid infusion device would generate an appropriate alert, alarm, or warning message, as described previously.

Adaptive Occlusion Detection

The force sensor 126 in the fluid infusion device 100 may also be used for purposes of occlusion detection. Most conventional occlusion detection schemes function by triggering an occlusion alarm when a certain preset threshold force is reached. For example, if the typical actuation force for a fluid reservoir is about one pound and the occlusion threshold is three pounds, a detected force that exceeds three pounds will initiate an alert or an alarm. In fluid infusion devices that are occluded, the force might increase by only fractions of a pound per unit of fluid (e.g., insulin) desired to be delivered. As a result, there can potentially be long wait times before an occlusion is actually confirmed.

In contrast, the technique described here is adaptive in nature, and occlusions can be determined prior to reaching the preset threshold by evaluating consecutive rates of change (slopes) of force. For example, assume that the typical force variation in a reservoir is only about 0.02 pound per unit (lb/U) over three or four delivery strokes or pulses. If an occlusion is present, the detected force might increase at a calculated rate of 0.30 lb/U over four consecutive pulses. If the fluid infusion device detects an occlusion, then an alarm might be generated and/or the occlusion force threshold might be adjusted downward by a certain amount. For example, if the normal occlusion threshold is three pounds, a detected occlusion condition might result in a downward adjustment of the occlusion threshold by thirty percent, resulting in an adjusted occlusion threshold of about two pounds. The adaptive approach enables the fluid infusion device to quickly detect an occlusion, relative to traditional methods that only use a static force threshold.

Figure 13:
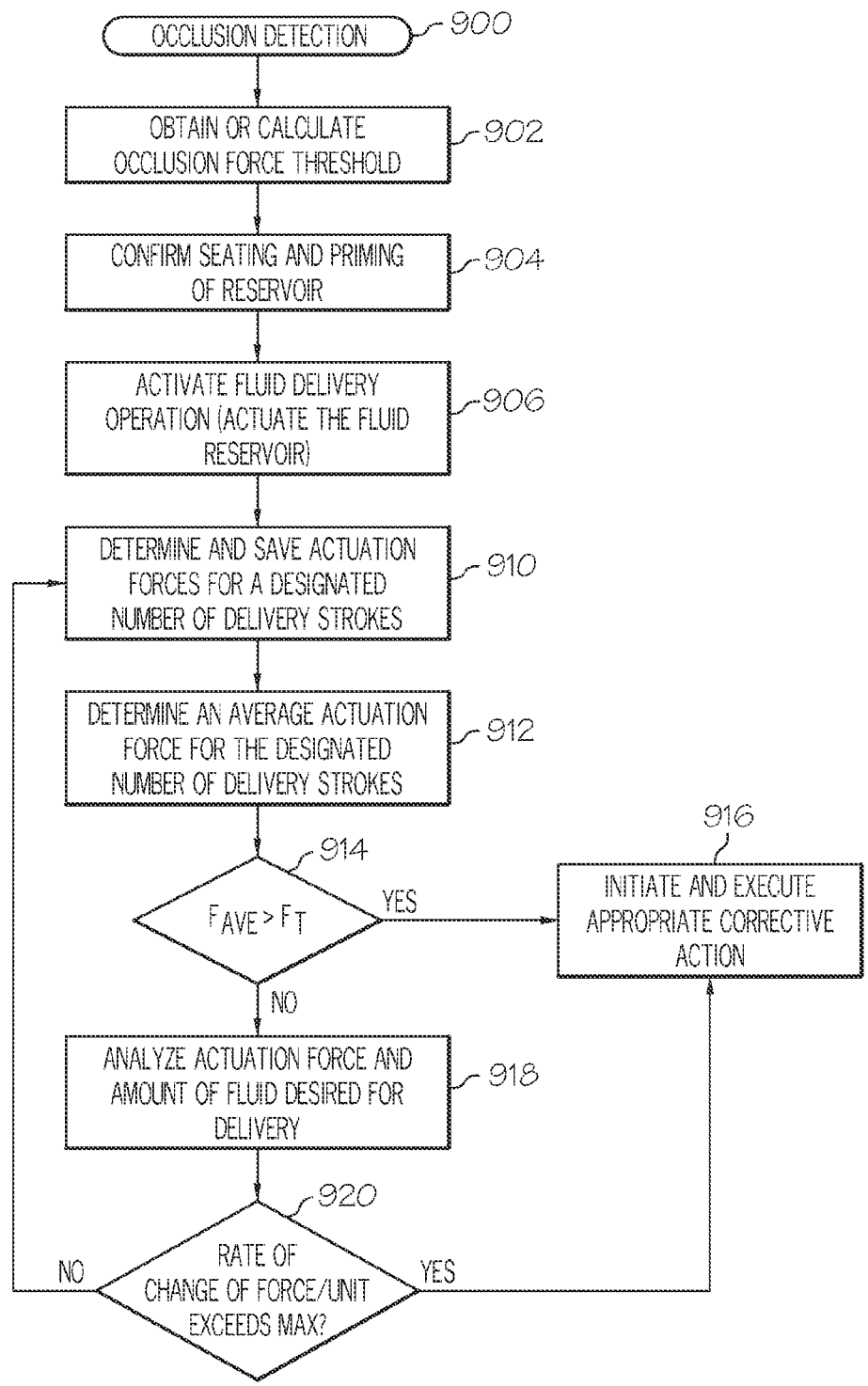
FIG. 13 is a flow chart that illustrates an embodiment of an occlusion detection process for a fluid infusion device.

FIG. 13 is a flow chart that illustrates an embodiment of an occlusion detection process 900 for a fluid infusion device, such as the fluid infusion device 100 described above. This embodiment of the process 900 employs an occlusion force threshold, which is consistent with traditional methodologies. Thus, the process 900 may begin by obtaining, calculating, or retrieving the occlusion force threshold (task 902). In typical implementations this occlusion force threshold is about 2.4 pounds, although the actual amount may vary from one embodiment to another.

In practice, the process 900 can be performed whenever a fluid reservoir is installed into the fluid infusion device. Accordingly, the process 900 may confirm the initial seating and/or priming of the fluid reservoir (task 904), and then activate a fluid delivery operation, which in turn actuates the fluid reservoir with the drive motor assembly (task 906). As described in more detail above, actuation of the fluid reservoir causes an amount of force to be imparted to the force sensor. Accordingly, the process 900 determines and saves actuation forces for a designated number of delivery strokes (task 910). This particular embodiment determines and saves actuation forces for a plurality of consecutive delivery strokes and then determines an average actuation force for the plurality of delivery strokes (task 912).

The process 900 may continue by comparing the average actuation force ($F_{AVE}$) to the occlusion force threshold ($F_T$) obtained at task 902. If the average actuation force is greater than the occlusion force threshold (query task 914), then the fluid infusion device initiates and executes appropriate corrective action (task 916). The corrective action taken by the fluid infusion device may include, without limitation, one or more of the actions described above for the process 200 (see FIG. 5). If, however, query task 914 determines that the average actuation force is not greater than the occlusion force threshold, then the process 900 continues.

The process may continue by analyzing the actuation force and the amount of fluid (typically expressed as a number or fraction of units) that is desired to be administered for delivery (task 918). As mentioned above, the process 900 analyzes the rate of change of a metric corresponding to the amount of detected force per unit of fluid (as commanded by the fluid infusion device). In this regard, the process 900 may compute this metric (e.g., in lb/U) in an ongoing manner during the fluid delivery operation. Moreover, the process 900 calculates the rate of change of this metric in an ongoing manner during the fluid delivery operation. Consequently, if the fluid infusion device determines that the rate of change exceeds a predetermined maximum value (query task 920), then the process 900 leads to task 916 and initiates appropriate corrective action. If, however, query task 920 determines that the rate of change does not exceed the maximum value, then the process 900 assumes that the fluid delivery path is not occluded. Accordingly, the process 900 returns to task 910 to continue monitoring actuation forces for the current fluid delivery operation (and for subsequent fluid delivery operations). The maximum tolerable rate of change may be a fixed value or it may be adaptive in nature. In typical embodiments, the maximum rate of change value will be about 1.0 lb/unit, although different values could be used depending upon the embodiment.

It should be appreciated that the process 900 may be practiced in conjunction with conventional occlusion detection schemes if so desired. For example, one or more of the occlusion detection approaches described in U.S. Pat. Nos. 6,485,465 and 7,621,893 (or modified versions thereof) could be employed with the process 900.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A device for delivering fluid to a user, the device comprising:
    a housing;
    a drive motor assembly in the housing to regulate delivery of fluid by actuating a piston of a fluid reservoir;
    a force sensor associated with the drive motor assembly to generate output levels in response to force imparted thereto, the force sensor located proximal to the drive motor assembly and between a proximal end of the drive motor assembly and a proximal end of the housing; and
    an electronics module coupled to the force sensor to process the output levels to determine operating health of the force sensor, and the electronics module:
    determines a rewind force measurement that indicates a rewind force imparted to the force sensor during a rewind operation;
    compares the rewind force measurement to a first force measurement threshold; and
    based on the comparison, initiates a corrective action based on the rewind force measurement being less than the first force measurement threshold.

2. The device of claim 1, wherein the corrective action is a user alert at the device when the rewind force measurement is less than the first force measurement threshold.

3. The device of claim 1, further comprising a memory element to store the first force measurement threshold.

4. The device of claim 1, wherein the electronics module:
    determines a delivery force imparted to the force sensor during a delivery operation; and
    initiates a corrective action when the delivery force is not within a specified range.

5. The device of claim 4, wherein the drive motor assembly includes a motor actuatable to drive the piston of the fluid reservoir, and the electronics module determines the delivery force imparted to the force sensor at each actuation of the motor during the delivery operation.

6. The device of claim 1, wherein the electronics module:
    determines a plurality of calibration rewind force measurements imparted to the force sensor over a calibration period;
    calculates a nominal rewind force from the plurality of calibration rewind force measurements; and
    initiates a corrective action when the nominal rewind force is not within a specified range.

7. The device of claim 1, wherein the electronics module processes the output levels to determine if the force sensor is damaged or in poor health.

8. The device of claim 1, wherein the electronics module:
    compares the rewind force measurement to a second force measurement threshold and initiates another corrective action, which is different than the corrective action, based on the rewind force measurement being greater than the second force measurement threshold.

* * * * *